United States Patent
Goto et al.

(10) Patent No.: US 11,452,688 B2
(45) Date of Patent: *Sep. 27, 2022

(54) TRANSDERMALLY ABSORBABLE BASE MATERIAL CONTAINING LIPID PEPTIDE COMPOUND

(71) Applicants: KYUSHU UNIVERSITY, Fukuoka (JP); NISSAN CHEMICAL INDUSTRIES, LTD., Tokyo (JP)

(72) Inventors: Masahiro Goto, Fukuoka (JP); Nobuhide Miyachi, Tokyo (JP); Takehisa Iwama, Funabashi (JP); Takayuki Imoto, Funabashi (JP)

(73) Assignees: KYUSHU UNIVERSITY, Fukuoka (JP); NISSAN CHEMICAL INDUSTRIES, LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/554,015

(22) Filed: Aug. 28, 2019

(65) Prior Publication Data

US 2019/0380949 A1 Dec. 19, 2019

Related U.S. Application Data

(62) Division of application No. 15/546,944, filed as application No. PCT/JP2016/052488 on Jan. 28, 2016, now abandoned.

(30) Foreign Application Priority Data

Jan. 28, 2015 (JP) ................................ 2015-014772

(51) Int. Cl.
| | | |
|---|---|---|
| *A61K 9/00* | (2006.01) | |
| *A61K 47/10* | (2017.01) | |
| *A61K 47/12* | (2006.01) | |
| *A61K 47/42* | (2017.01) | |
| *A61K 47/18* | (2017.01) | |
| *A61K 47/26* | (2006.01) | |
| *A61Q 19/00* | (2006.01) | |
| *A61K 9/06* | (2006.01) | |
| *A61K 38/28* | (2006.01) | |
| *A61K 31/728* | (2006.01) | |
| *A61K 8/02* | (2006.01) | |
| *A61K 8/34* | (2006.01) | |
| *A61K 8/36* | (2006.01) | |
| *A61K 8/60* | (2006.01) | |
| *A61K 8/64* | (2006.01) | |

(52) U.S. Cl.
CPC .......... *A61K 9/0014* (2013.01); *A61K 8/0229* (2013.01); *A61K 8/345* (2013.01); *A61K 8/361* (2013.01); *A61K 8/608* (2013.01); *A61K 8/64* (2013.01); *A61K 9/06* (2013.01); *A61K 31/728* (2013.01); *A61K 38/28* (2013.01); *A61K 47/10* (2013.01); *A61K 47/12* (2013.01); *A61K 47/183* (2013.01); *A61K 47/26* (2013.01); *A61K 47/42* (2013.01); *A61Q 19/00* (2013.01); *A61K 2800/10* (2013.01)

(58) Field of Classification Search
CPC .... A61K 9/0014; A61K 8/0229; A61K 8/345; A61K 8/361; A61K 8/608; A61K 8/64; A61K 47/26; A61K 47/10; A61K 47/12; A61K 47/42; A61K 2800/10; A61K 9/7023–7092; A61K 31/28; A61K 31/728; A61K 47/183; A61Q 19/00
See application file for complete search history.

(56) References Cited

U.S. PATENT DOCUMENTS

| 5,948,855 A | * | 9/1999 | Lin | ........................ | A61K 8/066 424/401 |
| 2005/0152993 A1 | | 7/2005 | De Oliveira | | |
| 2012/0064020 A1 | * | 3/2012 | Gempler | ................ | A61K 8/362 424/63 |

FOREIGN PATENT DOCUMENTS

| EP | 2 494 953 A1 | | 9/2012 |
| JP | 2 494 953 A1 | * | 5/2012 |

(Continued)

OTHER PUBLICATIONS

'Lauric Acid' in Handbook of Pharmaceutical Excipients Sixth Edition, Edited by RC Rowe, PJ Sheskey and ME Quinn; Pharmaceutical Press, pp. 383-385 (2009) (Year: 2009).*

(Continued)

*Primary Examiner* — Theodore R. Howell
(74) *Attorney, Agent, or Firm* — Oliff PLC

(57) ABSTRACT

A transdermally absorbable base material including: a lipid peptide compound including at least one of compound of Formula (1) below and the similar compounds or pharmaceutically usable salts thereof; a surfactant; a specific polyhydric alcohol; a fatty acid; and water,

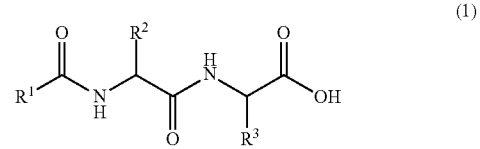

(1)

wherein $R^1$ is a $C_{9-23}$ aliphatic group; $R^2$ is a hydrogen atom or a $C_{1-4}$ alkyl group that optionally has a branched chain having a carbon atom number of 1 or 2; $R^3$ is a —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.

2 Claims, 5 Drawing Sheets

(56) References Cited

FOREIGN PATENT DOCUMENTS

| JP | 2012-518606 | A | 8/2012 |
|---|---|---|---|
| JP | 2015-051961 | A | 3/2015 |
| WO | 2009/005151 | A1 | 1/2009 |
| WO | 2009/005152 | A1 | 1/2009 |
| WO | 2010/094452 | A2 | 8/2010 |
| WO | 2011/052613 | A1 | 5/2011 |

OTHER PUBLICATIONS

Pavicic et al. in Journal of Drugs in Dermatology 10(9), 990-1000 (2011) (Year: 2011).*
Aungst, B.J. in Pharmaceutical Research 6(3) 244-247 (1989) (Year: 1989).*
Rastogi et al. in Pharmaceutical Development and Technology, 1:97-104, 2005 (Year: 2005).*
Murdan, Sudaxshina, "Organogels in drug delivery," Expert Opinion Drug Deliv., 2005, vol. 2, No. 3, pp. 1-17.
Kantaria et al., "Gelatin-stabilised microemulsion-based organogels: rheology and application in iontophoretic transdermal drug delivery," Journal of Controlled Release, 1999, vol. 60, pp. 355-365.
Chen et al., "Microemulsion-based hydrogel formulation of ibuprofen for topical delivery," International Journal of Pharmaceutics, 2006, vol. 315, pp. 52-58.
Suzuki et al., "Supramolecular Hydrogels Formed by L-Lysine Derivatives," Chemistry Letters, 2004, vol. 33, No. 11, pp. 1496-1497.
Jung et al., "Self-Assembly of a Sugar-Based Gelator in Water: Its Remarkable Diversity in Gelation Ability and Aggregate Structure," Langmuir, 2001, vol. 17, pp. 7229-7232.
Hamachi et al., "Solid-phase lipid synthesis (SPLS)-2: incidental discovery of organogelators based on artificial glycolipids," Tetrahedron Letters, 2001, vol. 42, pp. 6141-6145.
Hamachi et al., "Solid phase lipid synthesis (SPLS) for construction of an artificial glycolipid library," Chem. Commun., 2000, pp. 1281-1282.
Suzuki et al., "Supramolecular hydrogel formed by glucoheptonamide of L-Lysine: simple preparation and excellent hydrogelation ability," Tetrahedron, 2007, vol. 63, pp. 7302-7308.
Matsuzawa et al., "Assembly and Photoinduced Organization of Mono- and Oligopeptide Molecules Containing an Azobenzene Moiety," Advanced Functional Materials, 2007, vol. 17, pp. 1507-1514.
Apr. 12, 2016 International Search Report issued in International Patent Application No. PCT/JP2016/052488.
Apr. 12, 2016 Written Opinion of the International Searching Authority issued in International Patent Application No. PCT/JP2016/052488.
Miyachi et al.; "The development of a super molecular hydrogelator for cosmetic;" Fureguransu Janaru—Fragrance Journal; Oct. 2014; pp. 54-60; vol. 42, No. 10.
"GNPD—Day Moisturizer SPF 15;" Feb. 2014; Retrieved from URL: http://www.gndp.com/sinatra/recordpage/2323421/from_search/HP21GvxBk8/?page=1 [retrieved on Jul. 19, 2018].
Aug. 7, 2018 Search Report issued in European Patent Application No. 16743470.3.
Handbook of Pharmaceutical Excipients Sixth Edition, Edited by RC Rowe, PJ Sheskey and ME Quinn, Pharmaceutical Press, 917 pages, 2009.
Jul. 14, 2021 Office Action issued in Japanese Patent Application No. 2020-109040.

* cited by examiner

TRANSDERMALLY ABSORBABLE BASE MATERIAL CONTAINING LIPID PEPTIDE COMPOUND

This is a Division of application Ser. No. 15/546,944 filed Jul. 27, 2017, which in turn is a National Stage Application of Application No. PCT/JP2016/052488 filed Jan. 28, 2016, which claims the benefit of Japanese Application No. 2015-014772 filed Jan. 28, 2015. The disclosure of the prior applications is hereby incorporated by reference herein in its entirety.

TECHNICAL FIELD

The present invention relates to a transdermally absorbable base material that contains a lipid peptide compound and is useful as a base material for transdermally absorbable formulation, and preferably relates to a stick-shaped transdermally absorbable base material and a premix for the transdermally absorbable base material.

BACKGROUND ART

Administration of active ingredients through transdermal absorption has advantages, such as being noninvasive and adjustable in amount of dose, and therefore is a widely employed approach, as well as oral administration and injection administration. Transdermally absorbable formulation generally employs an approach of blending a transdermal absorption enhancer with a transdermally absorbable base material in order to enhance absorption of the active ingredients.

In recent years, attention has been paid to application of a gelled substance using a microemulsion technology to the transdermally absorbable formulation, from the viewpoint that the active ingredients and the transdermal absorption enhancer having different hydrophilicity/hydrophobicity can be simultaneously blended, and that solubility and activity of the active ingredients can be expected to be improved. For example, a w/o microemulsion gel containing lecithin [Non-Patent Documents 1 and 2] and an o/w microemulsion gel containing a thickener, such as a carboxy polymer or xanthan gum, [Non-Patent Document 3] have been developed.

Hydrogels are useful as highly biocompatible gels because of using water as a medium, and are used in a wide range of fields, typically for daily commodities, such as paper diapers, cosmetics, and aromatic materials.

Examples of conventional hydrogels include polymer gels that are formed in such a manner that polymer chains are cross-linked to form a three-dimensional net structure, which in turn forms a noncovalent bond with a medium, such as water, and swells. In recent years, hydrogels each formed by self-assembly of a relatively low-molecular-weight organic compound have been found, and studied in various ways. Many developments have been made so far on low-molecular gelators that are amphiphilic compounds in each of which a long-chain alkyl group as a hydrophobic moiety is combined with a hydrophilic moiety. Examples of such low-molecular gelators include one in which the hydrophilic moiety is amino acid [Non-Patent Document 4], one in which the hydrophilic moiety is a peptide [Patent Documents 1 and 2], one in which the hydrophilic moiety is a monosaccharide or a polysaccharide [Non-Patent Documents 5 and 6], and one in which the hydrophilic moiety is a polyol [Non-Patent Document 7]. A low-molecular gelator has also been developed [Non-Patent Document 8] by using the fact that a peptide formed of valine easily takes a 3-sheet structure.

PRIOR ART DOCUMENTS

Patent Documents

Patent Document 1: International Publication No. 2009/005151 pamphlet
Patent Document 2: International Publication No. 2009/005152 pamphlet Non-Patent Documents
Non-Patent Document 1: S. Murdan, Expert Opin. Drug Deliv. 2(3), 489-505 (2005)
Non-Patent Document 2: S. Kantaria, G. D. Rees, and M. J. Lawrence, J. Controlled Release, 60, 355-365 (1999)
Non-Patent Document 3: H. Chen, X. Chang, D. Du, L. Li, H. Xu, and X. Yang, International J. Pharm., 315, 52-58 (2006)
Non-Patent Document 4: Suzuki Masahiro, Yumoto Mariko, Kimura Mutsumi, Shirai Hirofusa, and Hanabusa Kenji, Chemistry Letters, 33 (11), 1496-1497
Non-Patent Document 5: Jong Hwa Jung, Georeg John, Mitsutosish Mausda, Kaname Yoshida, Seiji Shinnkai, and Toshimi Shimizu Langumuir, 2001, 17, 7229-7232
Non-Patent Document 6: I. Hamachi, S. Kiyonaka, S. Shinkai, Tetrahedron Lett., 2001, 42, 6141. I. Hamachi, S. Kiyonaka, S. Shinkai, Chem, Commun., 2000, 1281
Non-Patent Document 7: Masahiro Suzuki, Sanae Owa, Hirofusa Shirai, and Kenji Hanabusa, Tetrahedron, 2007, 63, 7302-7308
Non-Patent Document 8: Yoko Matsuzawa, Katsuyuki Ueki, Masaru Yoshida, Nobuyuki Tamaoki, Tohru Nakamura, Hideki Sakai, and Masahiko Abe, Adv. Funct. Mater., 2007, 17, 1507-1514

SUMMARY OF THE INVENTION

Problem to be Solved by the Invention

Lots of the w/o and o/w microemulsion gels developed so far use a polymer compound as the gelator, and it has been pointed out that applying such gels to skin can cause stickiness or uneven spread (residue of the polymer compound) after a lapse of time.

If the transdermally absorbable formulation using the above-described microemulsion gel is applied to the skin, the transdermal absorbability of the active ingredients is also an issue.

It is an object of the present invention to provide a novel transdermally absorbable base material that uses a low-molecular gelator to improve not only a sense of use, but also the transdermal absorbability.

Means for Solving the Problem

As a result of intensive studies to solve the above problem, the present inventors have found that a base material useful as the transdermally absorbable base material expected to increase the amount of penetration of the active ingredients to the skin is provided by employing, as the transdermally absorbable base material, an aqueous gel obtained by blending together a lipid peptide compound serving as a gelator constituted by a low-molecular lipid peptide or a pharmaceutically usable salt thereof, a surfactant, a specific polyhydric alcohol, and a fatty acid, and thus completed the present invention.

Specifically, the present invention relates to, as a first aspect, a transdermally absorbable base material comprising a lipid peptide compound including at least one of compounds of Formulae (1) to (3) below or pharmaceutically usable salts thereof, a surfactant, 1,2-alkanediol or glycerin, at least one fatty acid, and water.

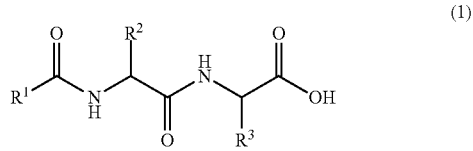

(wherein $R^1$ is a $C_{9-23}$ aliphatic group; $R^2$ is a hydrogen atom or a $C_{1-4}$ alkyl group that optionally has a branched chain having a carbon atom number of 1 or 2; $R^3$ is a —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

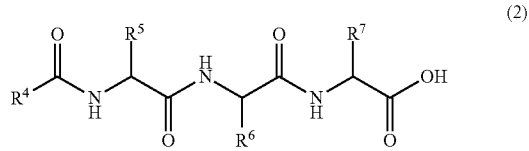

(wherein $R^4$ is a $C_{9-23}$ aliphatic group; $R^5$ to $R^7$ are each independently a hydrogen atom, a $C_{1-4}$ alkyl group that optionally has a branched chain having a carbon atom number of 1 or 2, or —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

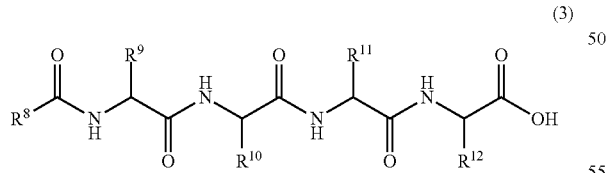

(wherein $R^8$ is a $C_{9-23}$ aliphatic group; $R^9$ to $R^{12}$ are each independently a hydrogen atom, a $C_{1-4}$ alkyl group that optionally has a branched chain having a carbon atom number of 1 or 2, or —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

The present invention relates to, as a second aspect, the transdermally absorbable base material according to the first aspect, in which the lipid peptide compound is a compound of Formula (1), wherein $R^1$ is a linear aliphatic group having a carbon atom number of 15; $R^2$ is a hydrogen atom; and $R^3$ is 4-imidazole methyl group.

The present invention relates to, as a third aspect, the transdermally absorbable base material according to the first or second aspect, being stick-shaped.

The present invention relates to, as a fourth aspect, the transdermally absorbable base material according to any one of the first to third aspects, further comprising at least one oleaginous base material.

The present invention relates to, as a fifth aspect, the transdermally absorbable base material according to any one of the first to fourth aspects, further comprising at least one organic acid.

The present invention relates to, as a sixth aspect, the transdermally absorbable base material according to any one of the first to fifth aspects, comprising, as the surfactant, at least one compound selected from the group consisting of ethylene glycol alkyl ethers, phospholipid, and polyglycerin fatty acid esters.

The present invention relates to, as a seventh aspect, the transdermally absorbable base material according to any one of the first to sixth aspects, further comprising polyoxyethylene (20) sorbitan monolaurate (CAS registry number 9005-64-5) as a surfactant.

The present invention relates to, as an eighth aspect, the transdermally absorbable base material according to any one of the first to seventh aspects, in which the fatty acid is stearic acid.

The present invention relates to, as a ninth aspect, the transdermally absorbable base material according to any one of the fifth to eighth aspects, in which the organic acid is at least one selected from the group consisting of oxalic acid, citric acid, and ascorbic acid.

The present invention relates to, as a tenth aspect, the transdermally absorbable base material according to any one of the first to ninth aspects, being used for cosmetics or pharmaceutical products.

The present invention relates to, as an eleventh aspect, a premix for a transdermally absorbable base material, the premix comprising a lipid peptide compound including at least one of compounds of Formulae (1) to (3) below or pharmaceutically usable salts thereof, a surfactant, 1,2-alkanediol or glycerin, and at least one fatty acid.

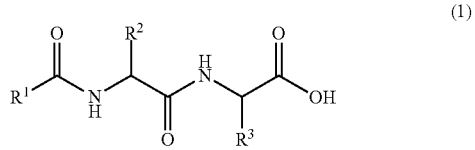

(wherein $R^1$ is a $C_{9-23}$ aliphatic group; $R^2$ is a hydrogen atom or a $C_{1-4}$ alkyl group that optionally has a branched chain having a carbon atom number of 1 or 2; $R^3$ is a —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

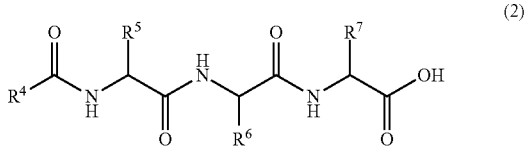

(2)

(wherein $R^4$ is a $C_{9-23}$ aliphatic group; $R^5$ to $R^7$ are each independently a hydrogen atom, a $C_{1-4}$ alkyl group that optionally has a branched chain having a carbon atom number of 1 or 2, or —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

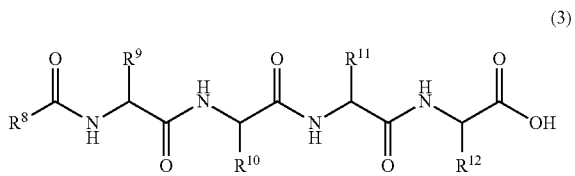

(3)

(wherein $R^8$ is a $C_{9-23}$ aliphatic group; $R^9$ to $R^{12}$ are each independently a hydrogen atom, a $C_{1-4}$ alkyl group that optionally has a branched chain having a carbon atom number of 1 or 2, or —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.)

Effects of the Invention

A transdermally absorbable base material of the present invention employs a composition of an aqueous gel containing a gelator (lipid peptide compound), a surfactant, a specific polyhydric alcohol, and a fatty acid so as to be useful as a transdermally absorbable base material that is excellent in the transdermal absorbability thereof when active ingredients, such as hyaluronic acid, are blended therewith.

The lipid peptide compound contained in the transdermally absorbable base material of the present invention is a very safe artificial low-molecular compound constituted by only fat and peptides. The compound can form an aqueous gel without using, for example, a cross-linking agent that is needed for forming a conventionally developed synthetic polymer gel, and consequently does not cause problems, such as residual unreacted substances, including, for example, an unreacted cross-linking agent in the obtained transdermally absorbable base material.

Moreover, various ingredients contained as additives in the transdermally absorbable base material of the present invention are additives generally used as additives for foods, cosmetics, and pharmaceutical products.

That is, the transdermally absorbable base material of the present invention has high biological safety, and is very useful for the applications described above, in particular, from the viewpoint of high safety required for materials for, for example, medical or cosmetic use.

Furthermore, the transdermally absorbable base material of the present invention is expected be a base material that gives a high cooling sensation and spreads well without being folded or deformed when applied to human skin or the like, and therefore is very useful as a base material for cosmetics or pharmaceutical products, and in particular, as a stick-shaped transdermally absorbable base material.

In addition, the present invention can provide a premixed raw material suitable for the transdermally absorbable base material described above.

Using the premix mentioned above allows the present invention to provide the transdermally absorbable base material in a gel state suitable for the stick-shaped base material, particularly even if an organic acid, such as ascorbic acid, is blended in a large amount.

MODES FOR CARRYING OUT THE INVENTION

Figure 1:
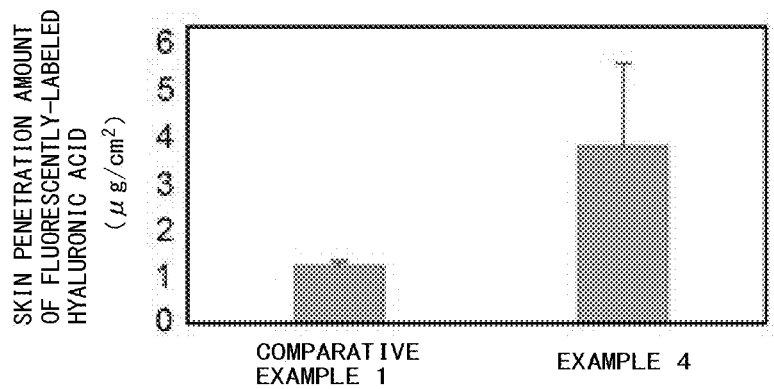
FIG. 1 is a diagram illustrating amounts of fluorescently-labeled hyaluronic acid in extracted solutions of skin after a skin permeability test (Example 5) conducted using transdermally absorbable base materials (gels) prepared in Examples 2 to 4 and Comparative Example 1.

The present invention relates to a transdermally absorbable base material that contains a lipid peptide compound including at least one of compounds of Formulae (1) to (3) below or pharmaceutically usable salts thereof, a surfactant, a specific polyhydric alcohol, a fatty acid, and water, and contains, as desired, an oleaginous base material, an organic acid, and other additives.

The present invention also relates to a premix for the transdermally absorbable base material containing the lipid peptide compound, the surfactant, the specific polyhydric alcohol, the fatty acid mentioned above.

The transdermally absorbable base material of the present invention is suitable for cosmetics or pharmaceutical products, and in particular, can be suitably used as a stick-shaped transdermally absorbable base material (hereinafter, also called a stick-shaped base material). In the present invention, the stick-shaped base material refers to a bar-like base material that retains a bar-like shape and has a strength enabling application to, for example, skin.

The components will be described below.

[Lipid Peptide Compound]

The lipid peptide compound used in the transdermally absorbable base material and the premix therefor of the present invention can be any of compounds (lipid peptides) of Formulae (1) to (3) below or a pharmaceutically usable salt thereof (a low-molecular compounds having a lipid moiety serving as a hydrophobic moiety and a peptide moiety serving as a hydrophilic moiety).

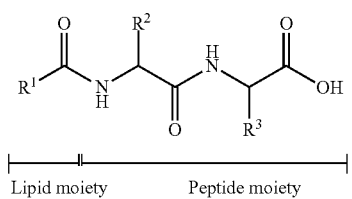

(1)

In Formula (1) above, $R^1$ is a $C_{9-23}$ aliphatic group, and preferably $R^1$ is a linear aliphatic group having a carbon atom number of 11 to 23, and optionally having 0 to 2 unsaturated bonds.

Specific examples of the lipid moiety (acyl group) constituted by $R^1$ and adjacent carbonyl group include lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidoyl group, eicosylcarbonyl group, behenoyl group, erucanoyl group, docosylcarbonyl group, lignoceyl group, and nervonoyl group. Among them, lauroyl group, myristoyl group, palmitoyl group, margaroyl group, stearoyl group, oleoyl group, elaidoyl group, and behenoyl group are particularly preferable.

In Formula (1) above, $R^2$ contained in the peptide moiety is a hydrogen atom or a $C_{1-4}$ alkyl group that optionally has a branched chain having a carbon atom number of 1 or 2.

The above-mentioned $C_{1-4}$ alkyl group that optionally has the branched chain having a carbon atom number of 1 or 2 refers to the alkyl group that has a $C_{1-4}$ main chain and optionally has the branched chain having a carbon atom number of 1 or 2, and specific examples thereof include methyl group, ethyl group, n-propyl group, i-propyl group, n-butyl group, i-butyl group, sec-butyl group, and tert-butyl group.

$R^2$ described above is preferably a hydrogen atom or a $C_{1-3}$ alkyl group that optionally has a branched chain having a carbon atom number of 1, and is more preferably a hydrogen atom.

The $C_{1-3}$ alkyl group that optionally has the branched chain having a carbon atom number of 1 refers to the alkyl group that has a $C_{1-3}$ main chain and optionally has the branched chain having a carbon atom number of 1, and specific examples thereof include methyl group, ethyl group, n-propyl group, i-propyl group, i-butyl group, and sec-butyl group. Among them, methyl group, i-propyl group, i-butyl group, and sec-butyl group are preferable.

In Formula (1) above, $R^3$ is a —$(CH_2)_n$—X group. In the —$(CH_2)_n$—X group mentioned above, n is a number of 1 to 4, and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms.

In the —$(CH_2)_n$—X group that is $R^3$ described above, X is preferably amino group, guanidino group, carbamoyl group (—$CONH_2$ group), pyrrole group, imidazole group, pyrazole group, or indole group, and is more preferably imidazole group. In the —$(CH_2)_n$—X group mentioned above, n is preferably 1 or 2, and is more preferably 1.

Accordingly, the above-described —$(CH_2)_n$—X group is preferably aminomethyl group, 2-aminoethyl group, 3-aminopropyl group, 4-aminobutyl group, carbamoylmethyl group, 2-carbamoyl ethyl group, 3-carbamoyl butyl group, 2-guanidino ethyl group, 3-guanidino butyl group, pyrrole methyl group, 4-imidazole methyl group, pyrazolemethyl group, or 3-indole methyl group, more preferably 4-aminobutyl group, carbamoylmethyl group, 2-carbamoyl ethyl group, 3-guanidino butyl group, 4-imidazole methyl group, or 3-indole methyl group, and still more preferably 4-imidazole methyl group.

In the compound of Formula (1) above, a particularly preferable lipid peptide as the lipid peptide compound is one of compounds listed below that is formed of a lipid moiety and a peptide moiety (amino acid assembly moiety). Amino acids are abbreviated as follows: alanine (Ala), asparagine (Asn), glutamine (Gln), glycine (Gly), histidine (His), isoleucine (Be), leucine (Leu), lysine (Lys), tryptophan (Trp), and valine (Val). The compounds are as follows: lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, and lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, and myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, and palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

Examples of the most preferable of these compounds include lauroyl-Gly-His and lauroyl-Ala-His; myristoyl-Gly-His and myristoyl-Ala-His; palmitoyl-Gly-His and palmitoyl-Ala-His; and stearoyl-Gly-His and stearoyl-Ala-His.

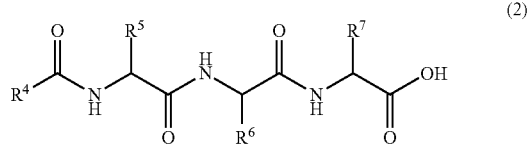

(2)

In Formula (2) above, s a $C_{9-23}$ aliphatic group, and preferable specific examples thereof include the same groups as those defined in $R^1$ described above.

In Formula (2) above, $R^5$ to $R^7$ are each independently a hydrogen atom, a $C_{1-4}$ alkyl group that optionally has a branched chain having a carbon atom number of 1 or 2, or —$(CH_2)_n$—X group, and at least one of $R^5$ to $R^7$ is preferably —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms. Preferable specific examples of $R^5$ to $R^7$ include the same groups as those defined in $R^2$ and $R^3$ described above.

In the compound of Formula (2) above, a preferable lipid peptide is one of the following compounds that is formed of a lipid moiety and a peptide moiety (amino acid assembly moiety): myristoyl-Gly-Gly-His, myristoyl-Gly-Gly-Gln, myristoyl-Gly-Gly-Asn, myristoyl-Gly-Gly-Trp, myristoyl-Gly-Gly-Lys, myristoyl-Gly-Ala-His, myristoyl-Gly-Ala-Gln, myristoyl-Gly-Ala-Asn, myristoyl-Gly-Ala-Trp, myristoyl-Gly-Ala-Lys, myristoyl-Ala-Gly-His, myristoyl-Ala-Gly-Gln, myristoyl-Ala-Gly-Asn, myristoyl-Ala-Gly-Trp, myristoyl-Ala-Gly-Lys, myristoyl-Gly-His-Gly, myristoyl-His-Gly-Gly, palmitoyl-Gly-Gly-His, palmitoyl-Gly-Gly-Gln, palmitoyl-Gly-Gly-Asn, palmitoyl-Gly-Gly-Trp, palmitoyl-Gly-Gly-Lys, palmitoyl-Gly-Ala-His, palmitoyl-Gly-Ala-Gln, palmitoyl-Gly-Ala-Asn, palmitoyl-Gly-Ala-Trp, palmitoyl-Gly-Ala-Lys, palmitoyl-Ala-Gly-His, palmitoyl-Ala-Gly-Gln, palmitoyl-Ala-Gly-Asn, palmitoyl-Ala-Gly-Trp, palmitoyl-Ala-Gly-Lys, palmitoyl-Gly-His-Gly, palmitoyl-His-Gly-Gly, lauroyl-Gly-Gly-His, and stearoyl-Gly-Gly-His.

Examples of the most preferable of these compounds include lauroyl-Gly-Gly-His, myristoyl-Gly-Gly-His, palmitoyl-Gly-Gly-His, palmitoyl-Gly-His-Gly, palmitoyl-His-Gly-Gly, and stearoyl-Gly-Gly-His.

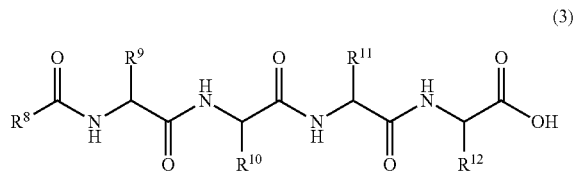

(3)

In Formula (3) above, $R^8$ is a $C_{9-23}$ aliphatic group, and preferable specific examples thereof include the same groups as those defined in $R^1$ described above.

In Formula (3) above, $R^9$ to $R^{12}$ are each independently a hydrogen atom, a $C_{1-4}$ alkyl group that optionally has a branched chain having a carbon atom number of 1 or 2, or —$(CH_2)_n$—X group, and at least one of $R^9$ to $R^{12}$ is preferably —$(CH_2)_n$—X group; n is a number of 1 to 4; and X is amino group, guanidino group, —$CONH_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms. Preferable specific examples of $R^9$ to $R^{12}$ include the same groups as those defined in $R^2$ and $R^3$ described above.

Accordingly, in the compound of Formula (3) above, examples of the preferable lipid peptide compound, in particular, the preferable lipid peptide include lauroyl-Gly-Gly-Gly-His, myristoyl-Gly-Gly-Gly-His, palmitoyl-Gly-Gly-Gly-His, palmitoyl-Gly-Gly-His-Gly, palmitoyl-Gly-His-Gly-Gly, palmitoyl-His-Gly-Gly-Gly, and stearoyl-Gly-Gly-Gly-His.

A particularly preferable compound among these lipid peptide compounds is a compound of Formula (1), wherein $R^1$ is a linear aliphatic group having a carbon atom number of 15; $R^2$ is a hydrogen atom; and $R^3$ is 4-imidazole methyl group, namely, a palmitoyl-Gly-His compound.

In the present invention, the blending amount of the lipid peptide compound with respect to the total mass of the obtained transdermally absorbable base material is, for example, from 0.01% to 30% by mass, preferably from 0.05% to 10% by mass, and more preferably from 0.1% to 10% by mass.

In the present invention, the blending amount of the lipid peptide compound with respect to the total mass of the obtained premix is, for example, from 5% to 20% by mass, and preferably from 10% to 20% by mass.

The lipid peptide compound used in the present invention includes at least one of the compounds (lipid peptides) of Formulae (1) to (3) above or pharmaceutically usable salts thereof. One or a combination of two or more of these compounds can be used as a hydrogelator.

[Surfactant]

A compound having a hydrophilic moiety having a betaine structure and a hydrophobic moiety in each molecule thereof (hereinafter, also called a betaine-based compound), ethylene glycol alkyl ethers, or polyglycerin fatty acid esters can be preferably used as the surfactant used in the transdermally absorbable base material or the premix therefor of the present invention.

Betaine-based compounds known as amphoteric surfactants can be used as the betaine-based compound described above. Examples of the known betaine-based compounds include N-alkyl-N,N-dimethyl amino acid betaines, such as lauryldimethyl aminoacetic acid betaine (lauryl betaine); fatty acid amide alkyl-N,N-dimethyl amino acid betaines, such as cocamidopropyl betaine and lauramidopropyl betaine; imidazoline-type betaines, such as sodium cocoamphoacetate and sodium lauroamphoacetate; alkyl sulfobetaines, such as lauryl hydroxy sulfobetaine and alkyl dimethyl taurines; sulfuric acid-type betaines, such as alkyl dimethyl amino ethanol sulfuric acid esters; and phosphoric acid-type betaines, such as alkyl dimethyl amino ethanol phosphoric acid esters.

Examples of the betaine-based compound described above include glycerophospholipids, such as phosphatidylcholine, phosphatidylethanolamine, phosphatidylserine, phosphatidylinositol, phosphatidylglycerol, diphosphatidylglycerol (cardiolipin), and phosphatidic acid; lysoglycerophospholipids, such as lysophosphatidylcholine (lysolecithin), lysophosphatidylethanolamine, lyzophosphatidylserine, lyzophosphatidylinositol, lyzophosphatidylglycerol, and lysophosphatidic acid; sphingophospholipids, such as sphingomyelin; and hydrogenated products thereof. These phospholipids may be those derived from animals and plants, such as soybeans and egg yolk, or may be synthesized by chemical or enzymatic methods.

Preferable examples of the betaine-based compound described above include lauryldimethyl aminoacetic acid betaine, lauramidopropyl betaine, lauryl hydroxy sulfobetaine, stearyl betaine, lysophosphatidylcholine (lysolecithin), lysophosphatidylethanolamine, lysophosphatidylserine, lyzophosphatidylinositol, lysophosphatidylglycerol, and lysophosphatidic acid, and more preferable examples thereof include lysophosphatidylcholine (lysolecithin).

Examples of the above-mentioned ethylene glycol alkyl ethers include polyoxyethylene lauryl ethers, polyoxyethylene palmitoyl ethers, and polyoxyethylene stearyl ethers. Among them, polyoxyethylene lauryl ethers and polyoxyethylene stearyl ethers are preferable.

Examples of the above-mentioned polyglycerin fatty acid esters include glycerin fatty acid partial esters, such as glyceryl stearate, glyceryl isostearate, glyceryl palmitate, glyceryl myristate, glyceryl oleate, coconut oil fatty acid glyceryl, mono-cottonseed oil fatty acid glycerin, glycerin monoerucate, glycerin sesquioleate, α, α'-oleic acid pyroglutamic acid glycerin, and glycerin monostearate malic acid; and polyglyceryl-2, -3, -4, -5, -6, -8, and -10 stearates, polyglyceryl-6 and -10 distearates, polyglyceryl-2 tristearates, polyglyceryl-10 decastearates, polyglyceryl-2, -3, -4, -5, -6, -8, and -10 isostearates, polyglyceryl-2 diisostearates (diglyceryl diisostearate), polyglyceryl-3 and -10 diisostearates, polyglyceryl-2 triisostearates, polyglyceryl-2 tetraisostearates, polyglyceryl-10 decaisostearates, polyglyceryl-2, -3, -4, -5, -6, -8, and -10 oleates, polyglyceryl-6 dioleates, polyglyceryl-2 trioleates, and polyglyceryl-10 decaoleates.

In the present invention, when the surfactant is classified based on a hydrophile-lipophile balance (HLB) value, the surfactant having an HLB value in the range of preferably 1.0 to 20.0, more preferably 2.0 to 17.0, and still more preferably 8.0 to 17.0 can be blended. Setting the HLB value of the surfactant in the above-described range can provide good dispersibility of an emulsion that can be constituted by hydrophilic and oleophilic components when the transdermally absorbable base material is prepared.

Specific examples of the surfactant in the above-described HLB range include sorbitan mono-fatty acid esters, such as sorbitan monolaurate ["Span 20" (registered trademark) manufactured by Wako Pure Chemical Industries Ltd., HLB=8.6]; and polyoxyethylene sorbitan fatty acid esters, such as polyoxyethylene (20) sorbitan monolaurates ["Tween 20" (registered trademark) manufactured by Wako Pure Chemical Industries Ltd., HLB=16.7], polyoxyethylene (4) sorbitan monostearates (HLB=9.6), polyoxyethylene (5) sorbitan monooleates (HLB=10.0), polyoxyethylene (4) sorbitan tristearates (HLB=10.5), polyoxyethylene (4) sorbitan trioleates (HLB=11.0), and polyoxyethylene (20) sorbitan monostearates (HLB=14.9).

Although partially overlapping with the above-mentioned compounds, examples of suitably usable surfactants having a hydrophile-lipophile balance (HLB) value of 10 to 12 include sorbitan isostearate, steareth-8, beheneth-10, laureth-5, ceteth-7, oleth-8, PEG-8 glyceryl isostearate, choleth-10, PEG-10BG isostearate, PEG-30 glyceryl triisostearate, PEG-30 glyceryl trioleate, PEG-30 trimethylolpropane triisostearate, PEG-30 hydrogenated castor oil laurate, PCA isostearate PEG-30 hydrogenated castor oil, octyldodeceth-10, PEG-12 dilaurate, sorbeth-40 tetraoleate, polyglyceryl-10 diisostearates, PEG-20 glyceryl diisostearate, PEG-8 isostearate, PEG-10 glyceryl isostearate, PEG-60 hydrogenated castor oil triisostearate, PPG-2-deceth-7, oleth-10, hydrogenated dimer dilinoleth-20, coconut fatty acid sorbitan, isosteareth-10, steareth-11, PEG-30 trimethylolpropane trimyristate, PEG-40 hydrogenated castor oil isostearate, PEG-40 hydrogenated castor oil PCA isostearate, laureth-7, isoceteth-10, ceteth-10, PEG-10 isostearate, PEG-10 stearate, PEG-10 oleate, PEG-10 glyceryl stearate, oleth-12, decyltetradeceth-15, choleth-15, PEG-16 dilaurate, PEG-30 hydrogenated castor oil, PEG-40 glyceryl triisostearate, PEG-40 glyceryl trioleate, PEG-40 trimethylolpropane triisostearate, and PEG-40 hydrogenated castor oil laurate.

In the present invention, the blending amount of the above-described surfactant with respect to the total mass of the obtained transdermally absorbable base material is, for example, from 0.1% to 20% by mass, preferably from 0.1% to 10% by mass, and more preferably from 0.1% to 5% by mass.

In the present invention, the blending amount of the above-described surfactant with respect to the total mass of the obtained premix is, for example, from 1% to 20% by mass, and preferably from 2% to 10% by mass.

The surfactant used in the present invention is at least one of the surfactants listed above. One or a combination of two or more of these surfactants can be used.

[1,2-Alkanediol or Glycerin]

The transdermally absorbable base material or the premix therefor of the present invention contains 1,2-alkanediol or glycerin.

1,2-alkanediol has a function to facilitate solubility of the lipid peptide compound, and specific examples thereof include 1,2-pentanediol, 1,2-hexanediol, 1,2-octanediol, and 1,2-decanediol. Among them, 1,2-pentanediol, 1,2-hexanediol, and 1,2-octanediol are preferable, and 1,2-pentanediol and 1,2-hexanediol are more preferable. The surfactant used in the present invention is at least one of the 1,2-alkanediols listed above. One or a combination of two or more of these 1,2-alkanediols can be used.

In addition to the 1,2-alkanediols listed above, glycerin is also suitably usable as a substance having the function to facilitate the solubility of the lipid peptide compound in the transdermally absorbable base material or the premix therefor of the present invention. Some commercial products of the above-described surfactant contain glycerin as a solvent. When such commercial products are used, the glycerin contained as an ingredient in the commercial products also acts so as to facilitate the solubility of the lipid peptide compound.

In the present invention, the blending amount of the 1,2-alkanediol or the glycerin with respect to the total mass of the obtained transdermally absorbable base material is, for example, from 0.1% to 20% by mass, preferably from 0.1% to 10% by mass, and more preferably from 0.1% to 5% by mass.

In the present invention, the blending amount of the 1,2-alkanediol or the glycerin with respect to the total mass of the obtained premix is, for example, from 2% to 20% by mass, and preferably from 2% to 10% by mass.

[Fatty Acid]

The fatty acid contained in the transdermally absorbable base material or the premix therefor of the present invention is preferably at least one selected from the group consisting of saturated and unsaturated $C_{10-20}$ fatty acids and salts thereof. Examples of the fatty acid include capric acid, undecanoic acid, lauric acid, tridecanoic acid, myristic acid, pentadecanoic acid, palmitic acid, margaric acid, and stearic acid. Among them, capric acid, lauric acid, myristic acid, palmitic acid, and stearic acid are more preferable, and stearic acid is particularly preferable.

The blending amount of the fatty acid used in the present invention is, for example, from 0.01% to 2.0% by mass, and preferably from 0.02% to 1.0% by mass, with respect to the total mass of the obtained transdermally absorbable base material.

In the present invention, the blending amount of the fatty acid with respect to the total mass of the obtained premix is, for example, from 0.5% to 5% by mass, and preferably from 0.5% to 3% by mass.

The fatty acid used in the present invention is at least one selected from the fatty acid group listed above. One or a combination of two or more of these fatty acids can be used.

[Oleaginous Base]

The transdermally absorbable base material of the present invention may further contain an oleaginous base material. The premix of the present invention can also contain the oleaginous base material.

Preferable examples of the oleaginous base used in the present invention include higher (polyhydric) alcohols, such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diol; aralkyl alcohols, such as benzyl alcohol and derivatives thereof; isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-heneicosanoic acid, long-chain branched fatty acids, dimeric acid, hydrogenated dimeric acid, and the like; hydrocarbons, such as liquid paraffin (mineral oil), heavy liquid isoparaffin, light liquid isoparaffin, an α-olefin oligomer, polyisobutenes, hydrogenated polyisobutenes, polybutenes, squalane, squalane derived from olive, squalene, vaseline, and solid paraffin; waxes, such as candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and ethylene-propylene copolymers; vegetable oils and fats, such as coconut oil, palm oil, palm kernel oil, safflower oil, olive oil, castor oil, avocado oil, sesame oil, tea seed oil, evening primrose oil, wheat germ oil, macadamia nut oil, hazelnut oil, candlenut oil, rose hip oil, meadowfoam oil, persic oil, tea tree oil, peppermint oil, corn oil, rapeseed oil, sunflower oil, wheat germ oil, linseed oil, cotton seed oil, soybean oil, peanut oil, rice bran oil, cacao butter, shea butter, hydrogenated coconut oil, hydrogenated castor oil, jojoba oil, and hydrogenated jojoba oil; animal oils and fats, such as beef tallow, milk fat, horse fat, egg yolk oil, mink oil, and turtle oil; animal waxes, such as spermaceti wax, lanolin, and orange roughy oil; lanolins, such as liquid lanolin, reduced lanolin, adsorption-purified lanolin, lanolin acetate, acetylated lanolin, hydroxylanolin, polyoxyethylene lanolins, lanolin fatty acid, hard lanolin fatty acid, lanolin alcohol, acetylated lanolin alcohol, and acetic acid (cetyl/lanolyl) esters; sterols, such as cholesterol, dihydrocholesterol, lanosterol, dihydrolanosterol, phytosterol, and cholic acid; sapogenins; saponins; sterol esters, such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, acyl sarcosine alkyl esters such as isopropyl N-lauroylsarcosinate, cholesteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branched fatty acid cholesteryl, and long-chain α-hydroxy fatty acid cholesteryl; lipid complexes, such as phospholipid-cholesterol complex and phospholipid-phytosterol complex; monoalcohol carboxylic acid esters, such as octyldodecyl myristate, hexyldecyl myristate, tetradecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyloctyl sebacate, diisobutyl adipate, dioctyl succinate, and triethyl citrate; oxy acid esters, such as cetyl lactate, diisostearyl malate, and hydrogenated castor oil monoisostearate; polyhydric alcohol fatty acid esters, such as glyceryl trioctanoate [glyceryl tri(2-ethylhexanoate)], glyceryl trioleate, glyceryl triisostearate, glyceryl diisostearate, glyceryl tri(caprylate/caprinate), glyceryl tri(caprylate/caprinate/myristate/stearate), hydrogenated rosin triglyceride (hydrogenated ester gum), rosin triglyceride (ester gum), glyceryl behenate/eicosanedienoate, trimethylolpropane trioctanoate, trimethylolpropane triisostearate, neopentyl glycol dioctanoate, neopentyl glycol dicaprinate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearates, polyglyceryl-10 nonaisostearates, polyglyceryl-8 deca(erucate/isostearate/ricinoleate), diglyceryl oligoesters (hexyldecanoate/sebacate), glycol distearate (ethylene glycol distearate), 3-methyl-1,5-pentanediol dineopentanoate, and 2,4-diethyl-1,5-pentanediol dineopentanoate; derivatives of dimer acids and dimer diols, such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, hydrogenated castor oil dimer dilinoleate, and hydroxyalkyl dimer dilinoleyl ethers; fatty acid alkanolamides, such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); silicones, such as dimethicone (dimethylpolysiloxane), highly polymerized dimethicones (highly polymerized dimethyl polysiloxanes), cyclomethicone (cyclic dimethylsiloxane, decamethylcyclopentasiloxane, or simply cyclopentasiloxane), phenyl trimethicone, diphenyl dimethicone, phenyl dimethicone, stearoxypropyldimethylamine, (aminoethylaminopropyl methicone/dimethicone) copolymers, dimethiconol, dimethiconol crosspolymers, silicone resins, silicone rubber, amino-modified silicones such as aminopropyl dimethicone and amodimethicone, cation-modified silicone, polyether-modified silicones such as dimethicone copolyols, polyglycerin-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine-based oil solutions such as perfluorodecane, perfluorooctane, and perfluoropolyethers.

In the present invention, the blending amount of the fatty acid with respect to the total mass of the obtained transdermally absorbable base material is, for example, from 1% to 50% by mass, preferably from 5% to 50% by mass, and more preferably from 10% to 50% by mass.

In the present invention, if the premix includes the oleaginous base material, the blending amount thereof is, for example, from 1% to 50% by mass, and preferably from 1% to 30% by mass, with respect to the total mass of the premix.

The above-described oleaginous base used in the present invention is at least one of the oleaginous bases listed above. One or a combination of two or more of these oleaginous bases can be used.

[Organic Acid]

The transdermally absorbable base material of the present invention may further contain an organic acid. The premix of the present invention can also contain the organic acid.

Examples of the organic acid include oxalic acid, ascorbic acid, citric acid, lactic acid, glycolic acid, succinic acid, acetic acid, malic acid, tartaric acid, and fumaric acid. Preferable examples thereof include ascorbic acid, citric acid, and lactic acid, and particularly preferable examples thereof include oxalic acid, ascorbic acid, and citric acid.

In the present invention, the blending amount of the organic acid with respect to the total mass of the obtained transdermally absorbable base material is, for example, from 0.5% to 50% by mass, and preferably from 0.5% to 30% by mass.

In the present invention, if the premix includes the organic acid, the blending amount thereof is, for example, from 1% to 20% by mass, and preferably from 1% to 10% by mass, with respect to the total mass of the premix.

[Other Additives]

The transdermally absorbable base material of the present invention can be blended, as needed, with additives generally usable as additives for cosmetics or additives for quasi-drugs. Examples of added ingredients, such as biologically active substances and functional substances, blended in the transdermally absorbable base material (solid base material for skin external application) of cosmetics or quasi-drugs include humectants, touch improvers, surfactants, transdermal absorption enhancers, polymers, thickeners/gelators, solvents/propellants, antioxidants, reductants, oxidants, preservatives, antimicrobe agents, bactericides, chelating agents, pH adjusters, acids, alkalis, powder, inorganic salts, ultraviolet absorbers, whitening agents, vitamins and derivatives thereof, hair growth drugs, blood circulation accelerators, stimulants, hormones, anti-wrinkle agents, anti-aging agents, tightening agents, cooling agents, warming agents, wound healing accelerators, irritation reducing agents, analgesics, cell activators, plant/animal/microbial extracts, antipruritic agents, corneum releasing/dissolving agents, antiperspirants, refrigerants, astringent agents, enzymes, nucleic acids, fragrances, dyestuffs, colorants, dyes, pigments, antiphlogistic agents, antiinflammatory agents, antiasthmatic agents, anti-chronic obstructive pulmonary disease agents, antiallergic agents, immunomodulators, anti-infective agents, and antifungal agents.

Preferable examples of the humectant and touch improver include polyols, such as glycerin, 1,3-butylene glycol (1,3-butanediol), propylene glycol, 3-methyl-1,3-butanediol, 1,3-propanediol, 2-methyl-1,3-propanediol, trimethylolpropane, pentaerythritol, hexylene glycol, diglycerin, polyglycerins, diethylene glycol, polyethylene glycols, dipropylene glycol, polypropylene glycols, and ethylene glycol-propylene glycol copolymers, and polymers of these polyols; glycol alkyl ethers, such as diethylene glycol monoethyl ether (ethoxy diglycol), ethylene glycol monoethyl ether, ethylene glycol monobutyl ether, and diethylene glycol dibutyl ether; water soluble esters, such as polyglyceryl-10 (eicosanedienoate/tetradecanedienoate) and polyglyceryl-10 tetradecanedienoates; sugar alcohols, such as sorbitol, xylitol, erythritol, mannitol, and maltitol; saccharides, such as glucose, fructose, galactose, mannose, threose, xylose, arabinose, fucose, ribose, deoxyribose, maltose, trehalose, lactose, raffinose, gluconic acid, glucuronic acid, cyclodextrins (α-, β-, and β-cyclodextrins, and modified cyclodextrins such as maltosylated cyclodextrin and hydroxyalkylated cyclodextrins), β-glucan, chitin, chitosan, heparin and derivatives thereof, pectin, arabinogalactan, dextrin, dextran, glycogen, ethyl glucoside, and polymers or copolymers of glucosylmethyl methacrylate, and derivatives of these saccharides; hyaluronic acid and sodium hyaluronate; sodium chondroitin sulfate; mucoitin sulfate, charonin sulfate, keratosulfate, and dermatan sulfate; Tremella fuciformis extracts and Tremella fuciformis polysaccharides; fucoidan; tuberosa polysaccharides or natural polysaccharides; organic acids, such as citric acid, tartaric acid, and lactic acid, and salts thereof; urea and derivatives thereof; 2-pyrrolidone-5-carboxylic acid and salts thereof, such as a sodium salt; amino acids, such as betaine (trimethylglycine), proline, hydroxyproline, arginine, lysine, serine, glycine, alanine, phenylalanine, tyrosine, β-alanine, threonine, glutamic acid, glutamine, asparagine, aspartic acid, cysteine, methionine, leucine, isoleucine, valine, tryptophan, histidine, and taurine, and salts of these amino acids; protein peptides, such as collagen, fish-derived collagen, atelocollagen, gelatin, elastin, collagen-decomposed peptide, hydrolyzed collagen, hydroxypropylammonium chloride-hydrolyzed collagen, elastin-decomposed peptide, keratin-decomposed peptide, hydrolyzed keratin, conchiolin-decomposed peptide, hydrolyzed conchiolin, silk protein-decomposed peptide, hydrolyzed silk, lauroyl-hydrolyzed silk sodium, soybean protein-decomposed peptide, wheat-protein decomposed peptide, hydrolyzed wheat protein, casein-decomposed peptide, and acylated peptide, and derivatives of these protein peptides; acylated peptides, such as palmitoyl oligopeptide, palmitoyl pentapeptide, and palmitoyl tetrapeptide; silylated peptides; culture solution of lactic acid bacteria, yeast extract liquid, eggshell membrane protein, mucin from bovine submaxillary gland, hypotaurine, sesame lignan glycoside, glutathione, albumin, and milk serum; choline chloride and phosphorylcholine; animal/plant extracted components, such as placenta extract liquid, elastin, collagen, aloe extract, hamamelis water, loofah water, chamomilla extract, licorice extract, comfrey extract, silk extract, chestnut rose extract, yarrow extract, eucalyptus extract, and melilot extract; and ceramides, such as natural ceramides (types 1, 2, 3, 4, 5, and 6), hydroxyceramide, pseudo-ceramide, sphingoglycolipid, and extracts containing ceramide or ceramide saccharide.

Preferable examples of the surfactant include anionic surfactants, nonionic surfactants, cationic surfactants, amphoteric surfactants, and polymeric surfactants. Preferable examples of the surfactant are as follows. Preferable examples of the anionic surfactants include salts of fatty acids, such as potassium laurate and potassium myristate; alkyl sulfates, such as sodium lauryl sulfate, triethanolamine lauryl sulfate, and ammonium lauryl sulfate; polyoxyethylene alkyl sulfates, such as sodium laureth sulfate and triethanolamine laureth sulfate; salts of acyl-N-methylamino acids, such as sodium cocoyl methyl taurate, potassium cocoyl methyl taurate, sodium lauroyl methyl taurate, sodium myristoyl methyl taurate, sodium lauroyl methyl alaninate, sodium lauroyl sarcosinate, triethanolamine lauroyl sarcosinate, and sodium methylalanine lauroyl glutamate; salts of acylamino acids, such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates, such as sodium laureth acetate; succinic acid ester salts, such as sodium lauroyl monoethanolamide succinate; fatty acid alkanolamide ether carboxylates; acyl lactates; polyoxyethylene aliphatic amine sulfates; fatty acid alkanolamide sulfates; fatty acid glyceride sulfates, such as glycerin hydrogenated coconut oil fatty acid sulfate sodium salt; alkylbenzene polyoxyethylene sulfates; olefin sulfonates, such as sodium α-olefin sulfonate; alkyl sulfosuccinates, such as disodium lauryl sulfosuccinate and sodium dioctylsulfosuccinate; alkyl ether sulfosuccinates, such as disodium laureth sulfosuccinate, sodium monolauroyl monoethanolamide polyoxyethylene sulfosuccinates, and sodium lauryl polypropylene glycol sulfosuccinates; alkylbenzene sulfonates, such as sodium tetradecylbenzene sulfonate and triethanolamine tetradecylbenzene sulfonate; alkyl naphthalene sulfonates; alkane sulfonates; methyl ester salts of α-sulfofatty acids; acylisethionic acid salts; alkyl glycidyl ether sulfonates; alkyl sulfo acetates; alkyl ether phosphates, such as sodium laureth phosphate, sodium dilaureth phosphate, sodium trilaureth phosphate, and sodium monooleth phosphate; alkyl phosphates, such as potassium lauryl phosphate; sodium caseinate; alkyl aryl ether phosphates; fatty acid amide ether phosphates; phospholipids, such as phosphatidylglycerol, phosphatidylinositol, and phosphatidic acid; and silicone-based anionic surfactants, such as carboxylic acid-modified silicones, phosphoric acid-modified silicones, and sulfuric acid-modified silicones. Preferable examples of the nonionic surfactants include polyoxyethylene alkyl ethers having various numbers of added polyoxyethylenes, such as laureths (polyoxyethylene lauryl ethers), ceteths (polyoxyethylene cetyl ethers), steareths (polyoxyethylene stearyl ethers), beheneths (polyoxyethylene behenyl ethers), isostearths (polyoxyethylene isostearyl ethers), and octyldodeceths (polyoxyethylene octyldodecyl ethers); polyoxyethylene alkyl phenyl ethers; derivatives of castor oil and hydrogenated castor oil, such as polyoxyethylene hydrogenated castor oils, polyoxyethylene castor oils, polyoxyethylene hydrogenated castor oil monoisostearates, polyoxyethylene hydrogenated castor oil triisostearates, polyoxyethylene hydrogenated castor oil monopyroglutamate-monoisostearate-diesters, and polyoxyethylene hydrogenated castor oil maleates; polyoxyethylene phytosterols; polyoxyethylene cholesterols; polyoxyethylene cholestanols; polyoxyethylene lanolins; polyoxyethylene reduced lanolins; polyoxyethylene-polyoxypropylene alkyl ethers, such as polyoxyethylene-polyoxypropylene cetyl ethers, polyoxyethylene-polyoxypropylene 2-decyltetradecyl ethers, polyoxyethylene-polyoxypropylene monobutyl ethers, polyoxyethylene-polyoxypropylene hydrogenated lanolins, and polyoxyethylene-polyoxypropylene glycerin ethers; polyoxyethylene-polyoxypropylene glycols; (poly)glycerin polyoxypropylene glycols, such as PPG-9 diglyceryl; glycerin fatty acid partial esters, such as glyceryl stearate, glyceryl isostearate, glyceryl palmitate, glyceryl myristate, glyceryl oleate, coconut oil fatty acid glyceryl, mono-cottonseed oil fatty acid glycerin, glycerin monoerucate, glycerin sesquioleate, α, α'-oleic acid pyroglutamic acid glycerin, and glycerin monostearate malic acid; polyglycerin fatty acid esters, such as polyglyceryl-2, -3, -4, -5, -6, -8, and -10 stearates, polyglyceryl-6 and -10 distearates, polyglyceryl-2 tristearate, polyglyceryl-10 decastearates, polyglyceryl-2, -3, -4, -5, -6, -8, and -10 isostearates, polyglyceryl-2 diisostearates (diglyceryl diisostearate), polyglyceryl-3 and -10 diisostearates, polyglyceryl-2 triisostearates, polyglyceryl-2 tetraisostearates, polyglyceryl-10 decaisostearates, polyglyceryl-2, -3, -4, -5, -6, -8, and -10 oleates, polyglyceryl-6 dioleates, polyglyceryl-2 trioleates, and polyglyceryl-10 decaoleates; ethylene glycol mono-fatty acid esters, such as ethylene glycol monostearate; propylene glycol mono-fatty acid esters, such as propylene glycol monostearate; pentaerythritol partial fatty acid ester; sorbitol partial fatty acid ester; maltitol partial fatty acid ester; maltitol ether; sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; sugar derivative partial esters, such as sucrose fatty acid ester, methylglucoside fatty acid ester, and trehalose undecylenate; alkyl glucosides, such as caprylyl glucoside; alkylpolyglucosides; lanolin alcohol; reduced lanolin; polyoxyethylene fatty acid mono- and di-esters, such as polyoxyethylene distearates, polythylene glycol diisostearates, polyoxyethylene monooleates, and polyoxyethylene dioleates; polyoxyethylene propylene glycol fatty acid esters; polyoxyethylene glycerin fatty acid esters, such as polyoxyethylene monooleates such as polyoxyethylene glycerin monostearates, polyoxyethylene glycerin monoisostearates, and polyoxyethylene glycerin triisostearates; polyoxyethylene sorbitan fatty acid esters, such as polyoxyethylene sorbitan monolaurates, polyoxyethylene sorbitan monooleates, polyoxyethylene sorbitan monostearates, polyoxyethylene sorbitan monoolates, and polyoxyethylene sorbitan tetraoleates; polyoxyethylene sorbitol fatty acid esters, such as polyoxyethylene sorbitol monolaurates, polyoxyethylene sorbitol monooleates, polyoxyethylene sorbitol pentaoleates, and polyoxyethylene sorbitol monostearates; polyoxyethylene methylglucoside fatty acid esters; polyoxyethylene alkyl ether fatty acid esters; polyoxyethylene animal and plant oils and fats, such as polyoxyethylene sorbitol beeswaxes; alkyl glyceryl ethers, such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants, such as saponin and sophorolipid; polyoxyethylene fatty acid amides; fatty acid alkanolamides, such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut oil fatty acid methylethanolamide (cocamide methyl MEA); alkyldimethylamine oxides, such as lauramine oxide, cocamine oxide, stearamine oxide, and behenamine oxide; alkylethoxydimethylamine oxides; polyoxyethylene alkyl mercaptans; and silicone-based nonionic surfactants, such as polyether-modified silicones such as dimethicone copolyols, polysiloxane-oxyalkylene copolymers, polyglycerin-modified silicones, and sugar-modified silicones. Preferable examples of the cationic surfactants include alkyltrimethylammonium chlorides, such as behentrimonium chloride, steartrimonium chloride, cetrimonium chloride, and lauryltrimonium chloride; alkyltrimethylammonium bromides, such as steartrimonium bromide; dialkyldimethylammonium chlorides, such as distearyldimonium chloride and dicocodimonium chloride; fatty acid amido amines, such as stearamidopropyl dimethylamine and stearamidoethyl diethylamine, and salts thereof; alkyletheramines, such as stearoxypropyl dimethylamine, and salts or quaternary salts thereof; fatty acid amide-type quaternary ammonium salts, such as long-chain branched fatty acid (12 to 31) aminopropylethyldimethylammonium ethyl sulfate and lanolin fatty acid aminopropylethyldimethylammonium ethyl sulfate; polyoxyethylene alkylamines and salts or quaternary salts thereof; alkylamine salts; fatty acid amide guanidium salts; alkyl ether ammonium salts; alkyl trialkylene glycol ammonium salts; benzalkonium salts; benzethonium salts; pyridinium salts, such as cetylpyridinium chloride; imidazolinium salts; alkyl isoquinolinium salts; dialkyl morpholinium salts; polyamine fatty acid derivatives; and silicone-based cationic surfactants, such as amino-modified silicones such as aminopropyl dimethicone and amodimethicone, cation-modified silicones, cation-modified and polyether-modified silicones, and amino-modified and polyether-modified silicones. Preferable examples of the amphoteric surfactants include N-alkyl-N,N-dimethyl amino acid betaines, such as lauryl betaine (lauryldimethyl aminoacetic acid betaine); fatty acid amide alkyl-N,N-dimethyl amino acid betaines, such as cocamidopropyl betaine and lauramidopropyl betaine; imidazoline-type betaines, such as sodium cocoamphoacetate and sodium lauroamphoacetate; alkylsulfo betaines, such as alkyl dimethyl taurines; sulfuric acid-type betaines, such as alkyl dimethyl amino ethanol sulfuric acid esters; phosphoric acid-type betaines, such as alkyl dimethyl amino ethanol phosphoric acid esters; phospholipids, such as phosphatidylcholine, phosphatidylethanolamine, phosphatidylserine, sphingophospholipids, such as sphingomyelin, lysolecithin, hydrogenated soybean phospholipid, partially hydrogenated soybean phospholipid, hydrogenated egg yolk phospholipid, partially hydrogenated egg yolk phospholipid, and lecithin hydroxide; and silicone-based amphoteric surfactants. Preferable examples of the polymeric surfactants include polyvinyl alcohols, sodium alginate, starch derivatives, tragacanth gum, copolymers of alkyl acrylates or alkyl methacrylates, and various silicone-based surfactants.

Examples of the transdermal absorption enhancers include caprylic acid, capric acid, caproic acid, lauric acid, myristic acid, palmitic acid, stearic acid, isostearic acid, oleic acid, linoleic acid, linolenic acid, isopropyl myristate, isopropyl palmitate, lauryl alcohol, myristyl alcohol, oleyl alcohol, isostearyl alcohol, cetyl alcohol, lauric acid diethanolamide, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol monolaurate, propylene glycol monocaprylate, propylene glycol dicaprylate, polyethylene glycol monolaurates, polyethylene glycol monostearates, polyoxyethylene oleyl ethers, polyoxyethylene lauryl ethers, jojoba oil, squalane, olive oil, silicone oil, liquid paraffin, n-methyl-2-pyrrolidone, dl-camphor, and peppermint oil.

Preferable examples of the polymers, the thickeners, and the gelators include guar gum; locust bean gum; quince seed; carrageenan; galactan; gum arabic; tara gum; tamarind; furcellaran; karaya gum; sunset hibiscus; cara gum; tragacanth gum; pectin; pectic acid and salts thereof, such as a sodium salt; alginic acid and salts thereof, such as a sodium salt; mannan; starches of, for example, rice, corn, potato, and wheat; xanthan gum; dextran; succinoglucan; curdlan; hyaluronic acid and salts thereof; xanthan gum; pullulan, gellan gum; chitin; chitosan; agar; brown alga extract; chondroitin sulfate; casein; collagen; gelatin; albumin; celluloses and derivatives thereof, such as methyl cellulose, ethyl cellulose, hydroxyethyl cellulose, hydroxypropyl cellulose, hydroxypropylmethyl cellulose, carboxymethyl cellulose and salts such as a sodium salt thereof, methylhydroxypropyl cellulose, sodium cellulose sulfate, dialkyldimethyl ammonium sulfate celluloses, crystalline cellulose, and powdered cellulose; starch polymers, such as soluble starch, carboxymethyl starch, methylhydroxypropyl starch, and methyl starch; starch derivatives, such as starch hydroxypropyltrimonium chloride, and aluminum corn starch octenylsuccinate; alginic acid derivatives, such as sodium alginate and propylene glycol alginate ester; polyvinylpyrrolidones (PVP); polyvinylalcohols (PVA); vinylpyrrolidone-vinylalcohol copolymers; polyvinyl methyl ethers; polyethylene glycols; polypropylene glycols; polyoxyethylene-polyoxypropylene copolymers; amphoteric methacrylate ester copolymers, such as (methacryloyloxyethyl carboxybetaine/alkyl methacrylate) copolymers and (acrylate/stearyl acrylate/ethylamine oxide methacrylate) copolymers; (dimethicone/vinyldimethicone) crosspolymers; (alkyl acrylate/diacetone acrylamide) copolymers and AMP-(alkyl acrylate/diacetone acrylamide) copolymers; polyvinyl acetate partially saponified products; maleic acid copolymers; vinylpyrrolidone-dialkylaminoalkyl methacrylate copolymers; acrylic resin alkanolamines; polyesters and water-dispersible polyesters; polyacrylamides; copolymers of polyacrylate esters, such as ethyl polyacrylates; carboxyvinyl polymers; polyacrylic acids and salts thereof, such as a sodium salt; copolymers of acrylic acid and methacrylate esters; copolymers of alkyl acrylates and alkyl methacrylates; cationized celluloses, such as polyquaternium-10; diallyldimethylammonium chloride-acrylamide copolymers, such as polyquaternium-7; acrylic acid-diallyldimethylammonium chloride copolymers, such as polyquaternium-22; acrylic acid-diallyldimethylammonium chloride-acrylamide copolymers, such as polyquaternium-39; acrylic acid-cationized methacrylate ester copolymers; acrylic acid-cationized methacrylamide copolymers; copolymers of acrylic acid-methyl acrylate-methacrylamidepropyltrimethylammonium chloride, such as polyquaternium-47; methacrylate chloride choline ester polymers; cationized polysaccharides, such as cationized oligosaccharides, cationized dextran, and guar hydroxypropyltrimonium chloride; polyethyleneimines; cationic polymers; copolymers of polymers of 2-methacryloyloxyethyl phosphorylcholine and butyl methacrylate copolymers, such as polyquaternium-51; polymer emulsions, such as acrylic resin emulsions, ethyl polyacrylate emulsions, polyacrylalkyl ester emulsions, polyvinyl acetate resin emulsions, natural rubber latex, and synthetic latex; nitrocelluloses; polyurethanes and various copolymers thereof; various silicones; various silicone-based copolymers, such as acryl-silicone graft copolymers; various fluorine-based polymers; 12-hydroxystearic acid and salts thereof; dextrin fatty acid esters, such as dextrin palmitate and dextrin myristate; silicic anhydride; fumed silica (ultrafine particulate silicic anhydride); magnesium aluminum silicate; sodium magnesium silicate; metal soaps; dialkylphosphoric acid metal salts; bentonite; hectorite; organic modified clay minerals; saccharose fatty acid esters; and fructo-oligosaccharide fatty acid esters. Preferable examples among the above-listed examples include celluloses and derivatives thereof, alginic acid and salts thereof, polyvinylalcohols, hyaluronic acid and salts thereof, and collagen.

Preferable examples of the solvents and the propellants include lower alcohols, such as ethanol, 2-propanol (isopropyl alcohol), butanol, and isobutyl alcohol; glycols, such as propylene glycol, 1,3-butylene glycol, diethylene glycol, dipropylene glycol, and isopentyl diol; glycol ethers, such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters, such as ethylene glycol monoethyl ether acetate, diethylene glycol monoethyl ether acetate, and propylene glycol monoethyl ether acetate; glycol esters, such as diethoxyethyl succinate and ethylene glycol disuccinate; benzyl alcohol; benzyloxyethanol; propylene carbonate; dialkyl carbonates; acetone; ethyl acetate; N-methylpyrrolidone; toluene; fluorocarbon and next generation freon; LPG, dimethyl ether, and carbon dioxide.

Preferable examples of the antioxidants include tocopherol derivatives, such as tocopherol (vitamin E) and tocopherol acetate; BHT and BHA; gallic acid derivatives, such as propyl gallate; vitamin C (ascorbic acid) and/or derivatives thereof; erythorbic acid and derivatives thereof; sulfites, such as sodium sulfite; hydrogen sulfites, such as sodium hydrogensulfite; thiosulfates, such as sodium thiosulfate; metabisulfites; thiotaurine; hypotaurine; thioglycerol; thiourea; thioglycolic acid; and cysteine hydrochloride.

Preferable examples of the reducing agents include thioglycolic acid, cysteine, and cysteamine.

Preferable examples of the oxidants include a hydrogen peroxide solution, ammonium persulfate, sodium bromate, and percarbonic acid.

Preferable examples of the preservatives, the antimicrobe agents, and the bactericides include hydroxybenzoic acid and salts or esters thereof, such as methylparaben, ethylparaben, propylparaben, and butylparaben; salicylic acid; sodium benzoate; phenoxy ethanol; isothiazolinone derivatives, such as methyl-chloro-isothiazolinone and methyl-isothiazolinone; imidazolinium urea; dehydroacetic acid and salts thereof; phenols; halogenated bisphenols, such as triclosan; acid amides; quaternary ammonium salts; trichlorocarbanilide; zinc pyrithione; benzalkonium chloride; benzethonium chloride; sorbic acid; chlorhexidine; chlorhexidine gluconate; halocarban; hexachlorophene; hinokitiol; other phenols, such as phenol, isopropylphenol, cresol, thymol, parachlorophenol, phenylphenol, and phenylphenol sodium; phenylethyl alcohol; photosensitive elements; antibacterial zeolite; and silver ion.

Preferable examples of the chelating agents include edetates (ethylenediaminetetraacetates), such as EDTA, EDTA2Na, EDTA3Na, and EDTA4Na; hydroxyethylethylenediaminetriacetates, such as HEDTA3Na; pentetate (diethylenetriaminepentaacetate); phytic acid; phosphonic acids, such as etidronic acid and salts thereof, such as a sodium salt; polyamino acids, such as polyaspartic acids and polyglutamic acids; sodium polyphosphates; sodium metaphosphate; phosphoric acid; sodium citrate; citric acid; alanine; dihydroxyethylglycine; gluconic acid; ascorbic acid; succinic acid; and tartaric acid.

Preferable examples of the pH adjusters, the acids, and the alkalis include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propandiol, 2-amino-2-hydroxymethyl-1,3-propanediol, arginine, sodium hydroxide, potassium hydroxide, ammonia water, guanidine carbonate, and ammonium carbonate.

Preferable examples of the powder include inorganic powder having various sizes and shapes, such as mica, talc, kaolin, sericite, montmorillonite, kaolinite, isinglass, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal salts of tungstic acid, magnesium, zeolite, barium sulfate, baked calcium sulfate, calcium phosphate, fluorapatite, hydroxyapatite, ceramic powder, bentonite, smectite, clay, mud, metal soap (such as zinc myristate, calcium palmitate, aluminum stearate), calcium carbonate, red iron oxide, yellow iron oxide, black iron oxide, ultramarine blue, Prussian blue, carbon black, titanium oxide, fine particles and ultrafine particles of titanium oxide, zinc oxide, fine particles and ultrafine particles of zinc oxide, alumina, silica, fumed silica (ultrafine particulate silicic anhydride), mica titanium, fish scale guanine, boron nitride, photochromic pigment, synthetic fluorophlogopite, fine particles of compound powder, gold, and aluminum; inorganic powder such as powder hydrophobized or hydrophilized by treating the above-listed inorganic powder using various surface treating agents, such as silicone such as hydrogen silicone or cyclic hydrogen silicone, or otherwise, other silane, or a titanium coupling agent; and organic powder, surface-treated powder, and organic-inorganic compound powder having various sizes and shapes, such as starch, cellulose, nylon powder, polyethylene powder, poly(methyl methacrylate) powder, polystyrene powder, copolymer resin powder of styrene and acrylic acid, polyester powder, benzoguanamine resin powder, powder having layers of polyethylene terephthalates and poly(methyl methacrylate)s, powder having layers of polyethylene terephthalates, aluminum, and epoxy, urethane powder, silicone powder, and Teflon (registered trademark) powder.

Preferable examples of the inorganic salts include sodium chloride-containing salts, such as common salt, crude salt, rock salt, sea salt, and natural salt; potassium chloride; aluminum chloride; calcium chloride; magnesium chloride; bittern; zinc chloride; ammonium chloride; sodium sulfate; aluminum sulfate; aluminum potassium sulfate (alum); aluminum ammonium sulfate; barium sulfate; calcium sulfate; potassium sulfate; magnesium sulfate; zinc sulfate; iron sulfate; copper sulfate; sodium phosphates, such as 1Na, 2Na, and 3Na phosphoric acids; potassium phosphates; calcium phosphates; and magnesium phosphates.

Preferable examples of the ultraviolet absorbers include benzoic acid-based ultraviolet absorbers, such as p-aminobenzoic acid, p-aminobenzoic acid monoglycerin ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilic acid-based ultraviolet absorbers, such as homomenthyl N-acetylanthranilate; salicylic acid-based ultraviolet absorbers, such as salicylic acid and sodium salt thereof, amyl salicylate, menthyl salicylate, homomenthyl salicylate, octyl salicylate, phenyl salicylate, benzyl salicylate, and p-isopropanolphenyl salicylate; cinnamic acid-based ultraviolet absorbers, such as octyl cinnamate, ethyl-4-isopropyl-cinnamate, methyl 2,5-diisopropyl-cinnamate, ethyl 2,4-diisopropyl-cinnamate, methyl 2,4-diisopropyl-cinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethoxyethyl p-methoxycinnamate (cinoxate), cyclohexyl p-methoxycinnamate, ethyl α-cyano-β-phenyl-cinnamate, 2-ethylhexyl α-cyano-β-phenylcinnamate (octocrylene), glyceryl mono-2-ethylhexanoyl-di-p-methoxycinnamate, and ferulic acid and derivatives thereof; benzophenone-based ultraviolet absorbers, such as 2,4-dihydroxybenzophenone, 2,2'-dihydroxy-4-methoxybenzophenone, 2,2'-dihydroxy-4,4'-dimethoxybenzophenone, 2,2', 4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone 5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenon; 3-(4'-methylbenzylidene)-d, 1-camphor; 3-benzylidene-d, 1-camphor; 2-phenyl-5-methylbenzoxazole; 2,2'-hydroxy-5-methylphenylbenzotriazole;

2-(2'-hydroxy-5'-t-octylphenyl)benzotriazole; 2-(2'-hydroxy-5'-methylphenyl)benzotriazole; dibenzalazine; dianisoylmethane; 5-(3,3-dimethyl-2-norbornylidene)-3-pentan-2-one; dibenzoylmethane derivatives, such as 4-t-butylmethoxydibenzoylmethane; octyltriazone; urocanic acid derivatives, such as urocanic acid and ethyl urocanate; 2-(2'-hydroxy-5'-methylphenyl)benzotriazole; 1-(3,4-dimethoxyphenyl)-4,4-dimethyl-1,3-pentanedione; hydantoin derivatives, such as 2-ethylhexyl dimethoxybenzylidene dioxoimidazolidine propionate; phenylbenzimidazole sulfonic acid; terephthalylidene dicamphor sulfonic acid; drometrizole trisiloxane; methyl anthranilate; rutin and derivatives thereof; and orizanol and derivatives thereof.

Preferable examples of the whitening agents include hydroquinone glycoside, such as arbutin and a-arbutin, and esters thereof; ascorbic acid derivatives, such as ascorbic acid, ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbic acid alkyl ethers such as ascorbic acid ethyl ether, ascorbic acid glucoside such as ascorbic acid-2-glucoside and fatty acid ester thereof, ascorbic acid sulfate ester, and ascorbyl tocopheryl phosphate; kojic acid; ellagic acid, tranexamic acid and derivatives thereof; ferulic acid and derivatives thereof; placenta extract; glutathione; oryzanol; butyl resorcinol; and plant extracts, such as oil-soluble chamomilla extract, oil-soluble licorice extract, Tamarix chinensis extract, and Saxifraga sarmentosa extract.

Preferable examples of the vitamins and derivatives thereof include vitamin A, such as retinol, retinol acetate, and retinol palmitate; vitamin B group, such as thiamine hydrochloride salt, thiamine sulfate salt, riboflavin, riboflavin acetate, pyridoxine hydrochloride, pyridoxine dioctanoate, pyridoxine dipalmitate, flavin adenine dinucleotide, cyanocobalamin, folic acids, nicotinic acids, such as nicotinic-acid amide and benzyl nicotinate, and cholines; vitamin C group, such as ascorbic acid and salts thereof, such as a sodium salt; vitamin D; vitamin E group, such as α-, β-, γ-, and δ-tocopherols; other vitamins, such as pantothenic acid and biotin; ascorbic acid derivatives, such as ascorbic acid phosphate ester salts such as ascorbic acid phosphate ester sodium salt and ascorbic acid phosphate ester magnesium salt, ascorbic acid fatty acid esters such as ascorbic acid tetraisopalmitate ester, ascorbyl stearate, ascorbyl palmitate, and ascorbyl dipalmitate, ascorbic acid alkyl ethers such as ascorbic acid ethyl ether, ascorbic acid glucoside, such as ascorbic acid-2-glucoside and fatty acid ester thereof, and ascorbyl tocopheryl phosphate; vitamin derivatives, such as tocopherol derivatives such as tocopherol nicotinate, tocopherol acetate, tocopherol linoleate, tocopherol ferulate, and tocopherol phosphate ester; tocotrienol; and various vitamin derivatives.

Preferable examples of the hair growth drugs, the blood circulation accelerators, the stimulant include plant extracts/tinctures, such as Swertia japonica extract, capsicum tincture, ginger tincture, ginger extract, and cantharis tincture; capsaicin; nonylic acid vanillylamide; zingerone; ichthammol; tannic acid; borneol; cyclandelate; cinnarizine; tolazoline; acetylcholine; verapamil; cepharanthine; γ-oryzanol; vitamin E and derivatives thereof, such as tocopherol nicotinate and tocopherol acetate; γ-oryzanol; nicotinic acid and derivatives thereof, such as nicotinic amide, benzyl nicotinate ester, inositol hexanicotinate, and nicotinic alcohol; allantoin; photosensitive element 301; photosensitive element 401; carpronium chloride; pentadecanoic acid monoglyceride; flavanonol derivatives; stigmasterol or stigmastanol and glycoside thereof; and minoxidil.

Preferable examples of the hormones include estradiol, estrone, ethinylestradiol, cortisone, hydrocortisone, and prednisone. Preferable examples of other medical agents, such as the anti-wrinkle agents, the anti-aging agents, the tightening agents, the cooling agents, the warming agents, the wound healing accelerators, the irritation reducing agents, the analgesics, and the cell activators, include retinols, retinoic acids, and tocopheryl retinoate; lactic acid, glycolic acid, gluconic acid, fruit acid, salicylic acid, and, for example, glycosides and esterified compounds thereof; α- or 3-hydroxy acids and derivatives thereof, such as hydroxycapric acid, long-chain α-hydroxy fatty acid, and long-chain α-hydroxy fatty acid cholesteryl; γ-amino butyric acid and γ-amino-β-hydroxy butyric acid; carnitine; carnosine; creatine; ceramides and sphingosines; caffeine, xanthin, and the like, and derivatives thereof; antioxidants/active oxygen eliminating agents, such as coenzyme Q10, carotene, lycopene, astaxanthin, lutein, α-lipoic acid, platinum nanocolloid, and fullerenes; catechins; flavones, such as quercetin; isoflavones; gallic acid and ester sugar derivatives thereof; polyphenols, such as tannin, sesamin, protoanthocyanidin, chlorogenic acid, and apple polyphenols; rutin and derivatives thereof, such as glycosides thereof; hesperidin and derivatives thereof, such as glycosides thereof; lignan glycoside; substances related to licorice extract, such as glabridin, glabrene, liquiritin, and isoliquiritin; lactoferrin; shogaol and gingerol; fragrance materials, such as menthol and cedrol, and derivatives thereof; capsaicin, vanillin, and the like, and derivatives thereof; insect repellents, such as diethyltoluamide; complexes of biologically active substances and cyclodextrin.

Preferable examples of the plant/animal/microbial extracts include extracts, such as iris extract, Angelica keiskei extract, Thujopsis dolabrata extract, asparagus extract, avocado extract, Hydrangea serrata leaf extract, almond extract, althea extract, arnica extract, aloe extract, apricot extract, apricot kernel extract, Ginkgo biloba extract, Artemisia capillaris flower extract, fennel fruit extract, turmeric root extract, oolong tea extract, uva-ursi extract, Rosa multiflora fruit extract, Echinacea angustifolia leaf extract, isodon japonicus extract, Scutellaria baicalensis root extract, phellodendron bark extract, coptis rhizome extract, barley extract, panax ginseng extract, Hypericum erectum extract, Lamium album extract, Ononis spinosa extract, Nasturtium officinale extract, orange extract, dried sea water residues, sea weed extract, persimmon leaf extract, Pyracantha fortuneana fruit extract, hydrolyzed elastin, hydrolyzed wheat flour, hydrolyzed silk, pueraria root extract, Chamomile extract, oil-soluble Chamomile extract, carrot extract, Artemisia capillaris flower extract, oat extract, karkade extract, licorice extract, oil-soluble licorice extract, kiwi fruit extract, senecio extract, Auricularia auricula extract, cinchona bark extract, cucumber extract, paulownia tomentosa leaf extract, guanosine, guava extract, sophora root extract, gardenia extract, Sasa veitchii extract, Sophora angustifolia root extract, walnut extract, Japanese chestnut extract, grapefruit extract, clematis extract, black rice extract, brown sugar extract, black vinegar, chlorella extract, Mulberry extract, Gentiana lutea extract, Geranium nepalense sweet extract, black tea extract, yeast extract, Magnolia cortex extract, coffee extract, burdock extract, rice extract, fermented rice extract, fermented rice bran extract, rice germ oil, comfrey extract, collagen, Vaccinium vitis-idaea extract, Asiasarum root extract, bupleurum root extract, umbilical extract, saffron extract, salvia extract, Saponaria officinalis extract, Sasa bamboo grass extract, Crataegus cuneata fruit extract, Bombyx mori extract, Zanthoxylum piperitum peel extract, shiitake extract, Rehmannia chinensis extract, Lithospermum erythrorhizon root extract, Perilla extract, Tilia cordata flower extract, spiraea ulmaria flower extract, Jatoba extract, Paeonia lactiflora extract, Zingiber officinale extract, Acorus calamus root extract, Betula alba extract, Tremella fusiformis extract, Equisetum arvense extract, Stevia rebaudiana extract, fermentated products of Stevia rebaudiana, Tamarix chinensis extract, Hedera helix extract, Crataegus oxyacantha extract, Sambucus nigra extract, Achillea millefolium extract, Mentha piperita extract, sage extract, Malva sylvestris extract, Cnidium officinale root extract, Swertia japonica extract, mulberry bark extract, rhubarb extract, soybean extract, jujube extract, thyme extract, dandelion extract, lichen extract, tea extract, Eugenia caryophyllus flower extract, Imperata cylindrica root extract, citrus unshiu peel extract, tea tree oil, Rubus suavissimus extract, red pepper extract, angelica root extract, Calendula officinalis extract, peach kernel extract, bitter orange peel extract, Houttuynia cordata extract, tomato extract, fermented soybean extract, ginseng extract, garlic extract, Rosa canina fruit extract, hibiscus extract, Ophiopogon tuber extract, Nelumbo nucifera extract, parsley extract, birch extract, honey, hamamelis extract, Parietaria officinalis extract, Isodonis japonicus extract, bisabolol, Chamaecyparis obtusa extract, Lactobacillus bifidus extract, Eriobotrya japonica extract, coltsfoot extract, Petasites japonicus extract, Poria cocos extract, butcher's broom extract, grape extract, grape seed extract, propolis, Luffa cylindrica fruit extract, safflower extract, peppermint extract, Tilia platyphyllos flower extract, Paeonia suffruticosa root extract, Humulus lupulus extract, Rosa rugosa flower extract, pine cone extract, horse chestnut extract, Asian skunk-cabbage extract, Sapindus mukorossi peel extract, melissa extract, Cladosiphon okamuranus extract, peach extract, Centaurea cyanus flower extract, eucalyptus extract, Saxifraga sarmentosa extract, Citrus junos fruit extract, lily extract, coix seed extract, Artemisia princeps extract, lavender extract, green tea extract, eggshell membrane extract, apple extract, rooibos tea extract, lychee extract, lettuce extract, lemon extract, Forsythia extract, Astragalus sinicus extract, rose extract, rosemary extract, Anthemis nobilis flower extract, royal jelly extract, and Sanguisorba officinalis root extract, Examples of the antipruritic agents include diphenhydramine hydrochloride, chlorpheniramine maleate, camphor, and a substance-P inhibitor.

Examples of the corneum releasing/dissolving agents include salicylic acid, sulfur, resorcin, selenium sulfide, and pyridoxine.

Examples of the antiperspirants include chlorohydroxyaluminum, aluminum chloride, zinc oxide, and zinc p-phenolsulfonate.

Examples of the refrigerants include menthol and methyl salicylate.

Examples of the astringent agents include citric acid, tartaric acid, lactic acid, aluminum potassium sulfate, and tannic acid.

Examples of the enzymes include superoxide dismutase, catalase, lysozyme chloride, lipase, papain, pancreatin, and protease.

Preferable examples of the nucleic acids include ribonucleic acids and salts thereof, deoxyribo nucleic acids and salts thereof, and adenosine triphosphate disodium.

Preferable examples of the fragrances include synthetic fragrances, natural fragrances, and various blended fragrances, such as acetyl cedrene, amylcinnamaldehyde, allyl amyl glycolate, β-ionone, Iso E Super, isobutylquinoline, iris oil, irone, indole, ylang ylang oil, undecanal, undecenal, γ-undecalactone, estragole, eugenol, oakmoss, Opoponax resinoid, orange oil, eugenol, aurantiol, galaxolide, carvacrol, 1-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandal wood oil, santalol, cyclamen aldehyde, cyclopentadecanolide, methyl dihydrojasmonate, dihydromyrcenol, jasmine absolute, jasmine lactone, cis-jasmone, citral, citronellol, citronellal, cinnamon bark oil, 1,8-cineole, cinnamaldehyde, styrax resinoid, cedar wood oil, cedrene, cedrol, celery seed oil, thyme oil, damascone, damascenone, thymol, tuberose absolute, decanal, decalactone, terpineol, γ-terpinene, triplal, nerol, nonanal, 2,6-nonadienol, nonanolactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peruvian balsam, vetiver oil, vetiverol, peppermint oil, pepper oil, heliotropin, bergamot oil, benzyl benzoate, borneol, myrrh resinoid, musk ketone, methyl nonyl acetaldehyde, γ-methylionone, menthol, 1-menthol, 1-menthone, eucalyptus oil, β-ionone, lime oil, lavender oil, d-limonene, linalool, lyral, lilial, lemon oil, rose absolute, rose oxide, rose oil, rosemary oil, and various essential oils.

Preferable examples of the dyestuffs, the colorants, the dyes, the pigments include legal dyestuffs, such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes, such as Acid Red 14; basic dyes, such as Arianor Sienna Brown, Arianor Madder Red, Arianor Steel Blue, and Arianor Straw Yellow; nitro dyes, such as HC Yellow 2, HC Yellow 5, HC Red 3,4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments, such as titanium dioxide and zinc oxide; inorganic red-based pigments, such as iron oxide (red iron oxide) and iron titanate; inorganic brown-based pigments, such as γ-ferric oxide; inorganic yellow-based pigments, such as yellow iron oxide and ocher; inorganic black-based pigments, such as black iron oxide and low-order titanium oxide; inorganic violet-based pigments, such as mango violet and cobalt violet; inorganic green-based pigments, such as chromium oxide, chromium hydroxide, and cobalt titanate; inorganic blue-based pigments, such as ultramarine blue and Prussian blue; pearly pigments, such as titanium oxide-coated mica, titanium oxide-coated bismuth oxychloride, titanium oxide-coated talc, colored titanium oxide-coated mica, bismuth oxychloride, and fish scale guanine; metal powder pigments, such as aluminum powder, copper powder, and gold; surface-treated inorganic and metal powder pigments; organic pigments, such as a zirconium, barium, or aluminum lake; surface-treated organic pigments; natural dyestuffs and dyes, such as anthraquinones such as astaxanthin and alizarin, naphthoquinones such as anthocyanidin, β-carotene, catenar, capsanthin, chalcone, carthamin, quercetin, crocin, chlorophyll, curcumin, cochineal, and shikonin, bixin, flavones, betacyanidin, henna, hemoglobin, lycopene, riboflavin, and rutin; oxidation dye intermediates and couplers, such as p-phenylenediamine, toluene-2,5-diamine, o-, m-, or p-aminophenol, m-phenylenediamine, 5-amino-2-methylphenol, resorcin, 1-naphthol, and 2,6-diaminopyridine, and salts thereof; auto-oxidation type dyes, such as indoline; and dihydroxyacetone.

Preferable examples of the antiphlogistic agents and the antiinflammatory agents include glycyrrhizic acid and derivatives thereof, glycyrrhetic acid derivatives, salicylic acid derivatives, hinokitiol, guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, chlorpheniramine maleate, and plant extracts such as peach leaf extract and Artemisia princeps leaf extract.

Preferable examples of the antiasthmatic agents, the antichronic obstructive pulmonary disease agents, the antiallergic agents, and the immunomodulators include aminophylline, theophyllines, steroids (such as fluticasone and beclomethasone), leukotriene antagonists, thromboxane inhibitors, Intal, β-2 stimulants (such as formoterol, salmeterol, albuterol, tulobuterol, clenbuterol, epinephrine), tiotropium, ipratropium, dextromethorphan, dimemorfan, bromhexine, tranilast, ketotifen, azelastine, cetirizine, chlorpheniramine, mequitazine, tacrolimus, cyclosporine, sirolimus, methotrexate, cytokine regulating agents, interferon, omalizumab, and protein/antibody formulations.

Preferable examples of the anti-infective agents and the antifungal agents include oseltamivir, zanamivir, and itraconazole. The moisturizing base material can contain, in addition to the above-listed ingredients, known ingredients for cosmetics, pharmaceutical products, and foods, such as ingredients listed in, for example, the Japanese Standards of Cosmetic Ingredients, the Japanese Cosmetic Ingredients Codex, the Japan Cosmetic Industry Association's list of displayed names of ingredients, the International Cosmetic Ingredient Dictionary and Handbook (INCI Dictionary), the Japanese Standards of Quasi-drug Ingredients, the Japanese Pharmacopoeia, the Japanese Pharmaceutical Excipients, and the Japan's Specifications and Standards for Food Additives, and ingredients listed in patent publications and unexamined patent publications (including published and re-published Japanese translation of PCT international applications) of Japan and various other countries that are classified in classes A61K7 and A61K8 of the International Patent Classification (IPC), in known combinations and at known blending ratios or blending amounts.

[Production Method of Transdermally Absorbable Base Material (1)]

The transdermally absorbable base material of the present invention can be produced by mixing and stirring under heat, the lipid peptide compound including at least one of the compounds of Formulae (1) to (3) above or pharmaceutically usable salts thereof, the surfactant, the 1,2-alkanediol or the glycerin, at least one fatty acid, water, and furthermore, as desired, the oleaginous base material, the organic acid, and the other additives, and then leaving the mixture at rest to be cooled. The premix for the transdermally absorbable base material can be produced in this production process, as will be described later.

For example, the transdermally absorbable base material of the present invention is produced, as an example, by the following processes.

a) A process of blending the lipid peptide compound with the surfactant, the 1,2-alkanediol or the glycerin, at least one fatty acid, and water, and heating the mixture to prepare a solution or a dispersion liquid;

b) a process of adding the solution or the dispersion liquid to the water, and heating the mixture at a temperature of room temperature or higher and lower than 100° C.; and c) a process of cooling while stirring the mixture to a temperature lower than that in the heating process, and then leaving the mixture at rest to be cooled to be formed into a gelatinous solid (transdermally absorbable base material).

The oleaginous base material, the organic acid, and the other additives may be added in the preparation process of the solution or the dispersion liquid in the process a), or may be added in advance to the water to which the solution or the dispersion liquid is to be added in the process b). Moreover, the surfactant can be blended, instead of in the process a), in the subsequent process b).

The content of the water is preferably 50% by mass or higher and lower than 95% by mass with respect to the total mass of the obtained transdermally absorbable base material.

The content of the water is preferably 50% by mass or higher and lower than 80% by mass with respect to the total mass of the solution or the dispersion liquid obtained.

The heating temperature in the processes a) and b) is preferably from 50° C. to 90° C., and more preferably from 60° C. to 90° C., such as 80° C. The mixture is preferably stirred while being heated. While the time of heating and stirring in each of the processes depends on the types and blending amounts of the lipid peptide compound, the surfactant, and other ingredients used, the dissolution or dispersion can be normally completed in roughly 5 minutes to 50 minutes.

Subsequently to the processes a) and b), the mixture is cooled while being stirred until the liquid temperature reaches a temperature lower than that in the process b) (process c)). The cooling temperature in this process is, for example, roughly between room temperature and 80° C., between room temperature and 60° C., or between room temperature and 40° C.

[Production Methods of Premix and Transdermally Absorbable Base Material (2)]

The following describes a production method of the transdermally absorbable base material using the premix of the present invention.

As will be described in detail below, the premix is produced through the process a) of [Production method of transdermally absorbable base material (1)] described above.

<Production Method of Premix>

To produce the premix, first, the lipid peptide compound including at least one of the compounds of Formulae (1) to (3) above or pharmaceutically usable salts thereof, the surfactant, the 1,2-alkanediol or the glycerin, at least one fatty acid, and water are mixed together, and are heated to prepare the solution or the dispersion liquid. During the preparation of the solution or the dispersion liquid, the oleaginous base material, the organic acid, and the other additives can be added as desired.

The premix can be obtained by cooling the solution or the dispersion liquid.

The temperature of the above-described heating is preferably from 50° C. to 90° C., and more preferably from 60° C. to 90° C., such as 80° C. The mixture is preferably stirred while being heated. While the time of the heating (stirring) depends on the lipid peptide compound used, the types of the surfactant and other ingredients, and the blending amounts of these ingredients, the time is roughly 5 minutes to 50 minutes, after which the solution or the dispersion liquid in which the blended ingredients are dissolved or dispersed is obtained.

The solution or the dispersion liquid thus obtained is preferably cooled while being stirred to a temperature lower than the above-described heating temperature, for example, to a temperature roughly between room temperature and 80° C., between room temperature and 60° C., or between room temperature and 40° C., and then preferably stops being stirred to be left at rest.

The content of the water is preferably 50% by mass or higher and lower than 80% by mass with respect to the total mass of the obtained premix.

The premix thus obtained is useful as a premix for preparing the transdermally absorbable base material. The transdermally absorbable base material can be easily prepared by blending water and other effective ingredients with the premix, as will be described later.

<Production Method of Transdermally Absorbable Base Material Using Premix>

The transdermally absorbable base material can be produced through, for example, the following processes 1) to 3) using the premix of the present invention thus obtained.

1) A process of heating the premix at a temperature of room temperature or higher and lower than 100° C.;

2) a process of adding the above-described heated premix to an aqueous phase heated at a temperature of room temperature or higher and lower than 100° C., and mixing the mixture; and 3) a process of cooling the obtained mixture to form a gel.

The above-described aqueous phase contains water, can further contain the oleaginous base material, and may contain the organic acid and the other additives.

In the case of blending the organic acid with the transdermally absorbable base material, the transdermally absorbable base material blended with the organic acid can be produced through, for example, the following processes 4) to 7).

4) A process of heating the premix at a temperature of room temperature or higher and lower than 100° C.;

5) a process of adding the above-described heated premix to an aqueous phase heated at a temperature of room temperature or higher and lower than 100° C., and mixing the mixture;

6) a process of cooling the obtained mixture to form a gel; and 7) a process of adding a mixed solution of water and the organic acid to the above-described mixture and further mixing the resultant mixture during the above-described cooling process.

The above-described aqueous phase contains water, can further contain the oleaginous base material, and may further contain the other additives.

The heating temperature of the premix in the above-described processes 1) and 4) is preferably from 50° C. to 90° C., and more preferably from 60° C. to 90° C., such as 70° C. or 80° C. These processes are preferably performed while the stirring is performed. While the time of heating (stirring) in each of the processes depends on the types and blending amounts of the lipid peptide compound, the surfactant, and the other additives contained in the premix, the time is normally roughly 5 minutes to 50 minutes. These processes bring the premix into a uniformly dissolved state.

The heating temperature of the aqueous phase in the above-described processes 2) and 5) is preferably from 50° C. to 90° C., and more preferably from 60° C. to 90° C., such as 70° C. or 80° C. The aqueous phase is preferably heated while being stirred, particularly if the aqueous phase contains the other ingredients, such as the oleaginous base material. If the aqueous phase contains the oleaginous base material and the other ingredients, the heating (stirring) is preferably performed normally for roughly 5 minutes to 50 minutes until these ingredients are uniformly dissolved or dispersed. The heating temperature of the aqueous phase may be the same as that of the premix.

Subsequently, in each of the above-described processes 3) and 6), the mixture obtained in the previous process is cooled to form a gel. At this time, the mixture may be cooled while being stirred. If the mixture is cooled while being stirred, the mixture is preferably stirred until the cooling temperature reaches, for example, a temperature between room temperature and 80° C. or between room temperature and 60° C., such as roughly 60° C., and then preferably stops being stirred to be left at rest and cooled. The mixture preferably stops being stirred to be left at rest and cooled, particularly when the temperature is 50° C. or lower.

If the transdermally absorbable base material contains an organic acid such as ascorbic acid, the above-described process 6) (cooling process) includes a process of adding a mixed solution of water and the organic acid to the mixture and further mixing the resultant mixture.

In this process, the mixed solution of water and the organic acid to be added preferably has roughly the same temperature as that of the mixture to which the mixed solution is to be added so as to achieve uniform mixing. The mixed solution may contain the oleaginous base material and the other additives as desired, and may be heated (stirred) at an appropriate temperature until those ingredients are uniformly dissolved or dispersed.

For example, when the liquid temperature of the mixture has reached roughly 60° C. while being stirred in the above-described process 6), the mixed solution of water and the organic acid having the liquid temperature of roughly 60° C. is added to the mixture, and further mixed to make the system of mixture uniform. Then, the mixture preferably stops being stirred to be left at rest and cooled to obtain the gel (transdermally absorbable base material).

Also in the transdermally absorbable base material thus obtained using the premix, the blending amount of the water is preferably 50% by mass or higher and lower than 95% by mass with respect to the total mass of the transdermally absorbable base material.

EXAMPLES

The present invention will be described in detail by way of examples and test examples, but is not limited to these examples.

Synthesis Example 1: Synthesis of Lipid Peptide (N-palmitoyl-Gly-His)

A lipid peptide used as a gelator in examples was synthesized using a method described below.

Into a four-necked flask of 500 mL, 14.2 g (91.6 mmol) of histidine, 30.0 g (91.6 mmol) of N-palmitoyl-Gly-methyl, and 300 g of toluene were charged, and 35.3 g (183.2 mmol) of a 28% methanol solution of sodium methoxide as a base was added thereto. The mixture was heated to 60° C. in an oil bath, and stirred for 1 hour. Then, the oil bath was removed, and the solution was left standing to be cooled to 25° C. and was subjected to reprecipitation using 600 g of acetone to collect a solid by filtration. The solid obtained here was dissolved in a mixed solution of 600 g of water and 750 g of methanol. To the mixed solution, 30.5 mL (183.2 mmol) of 6N hydrochloric acid was added to neutralize the solution and precipitate a solid, which was then filtered. Then, the obtained solid was dissolved in a mixed solution of 120 g of tetrahydrofuran and 30 g of water at 60° C., and 150 g of ethyl acetate was added thereto. The mixture was cooled from 60° C. to 30° C. Then, the precipitated solid was collected by filtration. Furthermore, the obtained solid was dissolved in a solvent of 120 g of tetrahydrofuran and 60 g of acetonitrile. The solution was heated to 60° C., stirred for 1 hour, then cooled, and filtered. The solid thus obtained was washed with 120 g of water, filtered, and then dried under reduced pressure to obtain 26.9 g of white crystals of a free form of N-palmitoyl-Gly-His (hereinafter, also simply called Pal-GH) (at a yield of 65%).

Example 1: Preparation of Premix

The Pal-GH obtained in the synthesis example 1 above, 1,2-hexanediol, polyoxyethylene lauryl ether, stearic acid, and water were weigh out so as to form a composition (% by mass) illustrated in Table 1, and charged into a sample tube (No. 7 manufactured by Maruemu Corporation). The mixture was heated and stirred at 80° C. to obtain a Pal-GH dispersion liquid (premix). The stirring was performed at 200 rpm using LABORATORY HIGH MIXER manufactured by AS ONE Corporation.

TABLE 1

| Ingredient | Premix composition (% by mass) |
| --- | --- |
| Pal-GH | 10.0 |
| 1,2-hexanediol *1 | 4.0 |
| Polyoxyethylene lauryl ether *2 | 8.0 |
| Stearic acid *3 | 1.0 |
| Water | Rest |

*1 manufactured by ITO Inc.
*2 manufactured by Nikko Chemicals Co., Ltd. [product name: NIKKOL BL 4.2, POE (4.2) lauryl ether]
*3 manufactured by Kao Corporation [product name: S-98]

Examples 2 to 4 and Comparative Example 1: Preparation of Transdermally Absorbable Base Material Using Premix According to Table 2 below, Phase A (premix prepared in Example 1) was weighed out into a sample tube No. 5, and heated in a water bath (at a set temperature of 85° C.) to be uniformly dissolved.

The ingredients of Phase B were weighed out into another Maruemu sample tube No. 5 having therein a stirrer chip, and heated in a water bath (at a set temperature of 85° C.). Phase A was added to Phase B, mixed while being heated and stirred for roughly 30 seconds. Then, the mixture was cooled while being stirred until the liquid temperature reached roughly 60° C.

For each of Examples 2 and 3, the ingredients of Phase C were weighed out into still another sample tube No. 5, and heated to a liquid temperature of roughly 60° C. When the liquid temperature of mixture of Phase A and Phase B described above reached 60° C., Phase C having a liquid temperature of roughly 60° C. was added thereto, and the mixture was stirred for roughly 30 seconds, and then left at rest and cooled to be formed into a gel (transdermally absorbable base material).

For each of Example 4 and Comparative Example 1, after the liquid temperature reached roughly 60° C., the mixture was left at rest and cooled to be formed into a gel (transdermally absorbable base material).

TABLE 2

| | Ingredient (g) | Example 2 | Example 3 | Example 4 | Comparative Example 1 |
|---|---|---|---|---|---|
| Phase A | Premix | 5 | 5 | 50 | |
| | 1.0 wt % Carbopol *4 | | | | 50 |
| Phase B | Fluorescently-labeled 1.0 wt % hyaluronic acid aqueous solution *5 | 20 | 20 | 20 | 20 |
| | 1,3-butanediol *6 | 20 | 20 | | |
| | Squalane *7 | | 10 | | |
| | 1M NaOH *8 | | | | 2 |
| | 10% Tween 20 aqueous solution *9 | | 5 | | |
| | Water | 30 | 15 | 30 | 28 |
| Phase C | 40 wt % citric acid solution *10 | 25 | 25 | | |

*4 manufactured by Nikko Chemicals Co., Ltd.
*5 manufactured by Kewpie Corporation [product name: Hyalo-Oligo (registered trademark)]
*6 manufactured by Wako Pure Chemical Industries Ltd.
*7 manufactured by Wako Pure Chemical Industries Ltd. [product name: Squalane]
*8 manufactured by Nacalai Tesque, Inc. [product name: 1 mol/L-sodium hydroxide solution]
*9 manufactured by Tokyo Chemical Industry Co., Ltd. [product name: Tween #20]
*10 manufactured by Wako Pure Chemical Industries Ltd. [prepared using citric acid monohydrate]

Example 5: Skin Permeability Test of Transdermally Absorbable Base Material

Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

Figure 2:
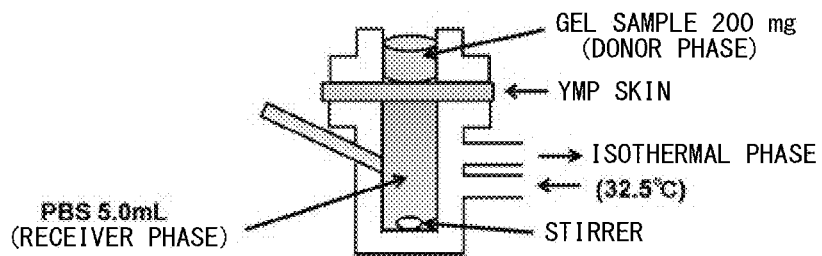
FIG. 2 is a conceptual diagram of a device used in the skin permeability test in Example 5.

To a receiver phase of a vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Example 4 and Comparative Example 1 was placed in the donor phase of the vertical Franz type diffusion cell (refer to FIG. 2).

The skin was taken out after 24 hours, and washed with an extractant [solution of PBS, acetonitrile, and methanol mixed at 2:1:1 (v/v/v)]. The liquid on the skin surface was wiped out with KimWipes (registered trademark). Then, the skin was cut into small pieces (16 pieces) with a utility knife, and put into a light-shielding microtube, to which 0.5 mL of the above-described extractant was added. The mixture was stirred with a vortex mixer for three hours, and fluorescently-labeled hyaluronic acid in the skin was extracted. The extracted solution thus obtained was filtered using a PTFE filter (0.45 μm), and then, the quantity of the fluorescently-labeled hyaluronic acid in the solution was determined using a fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 1 illustrates the results obtained.

As illustrated in FIG. 1, the results were obtained, showing that the transdermally absorbable base material of Example 4 surpasses the transdermally absorbable base material of Comparative Example 1 in transdermal absorption of hyaluronic acid by a factor of roughly 3.

In this way, the result shows that the transdermally absorbable base material of the present invention is useful as a transdermally absorbable base material excellent in the transdermal absorbability thereof when the active ingredients, such as hyaluronic acid, are blended therewith.

Moreover, as described below, the transdermal absorbability was tested for the transdermally absorbable base material of the present invention or transdermally absorbable base materials containing an oleaginous component (isopropyl myristate (IPM)) of the present invention when insulin was blended as an active ingredient. Commercially available insulin manufactured by Sigma-Aldrich Corporation and the following prepared insulin were used as the fluorescently-labeled insulin.

Preparation Example 1: Preparation of Fluorescently-Labeled Insulin Aqueous Solution Insulin/carbonic acid buffer (15 mg/mL) was prepared as described below. 30 mg of insulin (insulin from bovine pancreas (lot number: 016K1256) manufactured by Sigma-Aldrich Corporation) was dissolved in 2 mL of 0.1 M carbonic acid buffer (pH 9) over several days. 250 μL of FITC/DMSO (20 mg/mL) was prepared (FITC: fluorescein-5-isothiocyanate manufactured by Molecular Probes, Inc.). Under the shaded condition, a total of 250 μL of the FITC/DMSO solution was added 10 μL at a time while the insulin was slowly stirred. Under the shaded condition, the solution was reacted at 4° C. to 10° C. for roughly two nights. The solution was refined using a PD-10 column, and an FITC-labeled insulin aqueous solution was obtained. The protein density was calculated using a BCA assay; the FITC density was calculated using an absorbance method; and the labeling ratio was calculated.

With a labeling ratio of 0.733909, 3.334969 mg/ml of the FITC-labeled insulin aqueous solution was obtained.

Examples 6 and 7 and Comparative Example 2: Preparation of Transdermally Absorbable Base Material Using Premix According to Table 3 below, Phase A (premix prepared in Example 1) was weighed out into a sample tube No. 5, and heated in a water bath (at a set temperature of 85° C.) to be uniformly dissolved.

The ingredients of Phase B were weighed out into another Maruemu sample tube No. 5 having therein a stirrer chip, and heated in a water bath (at a set temperature of 85° C.). Phase A was added to Phase B, mixed while being heated and stirred for roughly 30 seconds. Then, the mixture was cooled while being stirred until the liquid temperature reached roughly 60° C.

For each of Examples 6 and 7, the ingredients of Phase C were weighed out into still another sample tube No. 5, and heated to a liquid temperature of roughly 60° C. When the liquid temperature of (Phase A+Phase B) described above reached 60° C., Phase C having a liquid temperature of roughly 60° C. was added thereto, and the mixture was stirred for roughly 30 seconds, and then left at rest and cooled to be formed into a gel (transdermally absorbable base material). Each of the prepared transdermally absorbable base materials contains 0.1% by mass of the fluorescently-labeled insulin (FITC-labeled insulin).

For Comparative Example 2, after the liquid temperature reached roughly 60° C., the mixture was left at rest and cooled to be formed into a gel (transdermally absorbable base material).

TABLE 3

|  | Ingredient (g) | Example 6 | Example 7 | Comparative Example 2 |
|---|---|---|---|---|
| Phase A | Premix | 5 | 5 |  |
|  | 1.0 wt % Carbopol *[11] |  |  | 50 |
| Phase B | 1 wt % FITC-labeled insulin aqueous solution *[12] | 10 | 10 | 10 |
|  | 1,3-butanediol *[13] | 20 | 20 |  |
|  | IPM *[14] |  | 10 |  |
|  | 1M NaOH *[15] |  |  | 0.5 |
|  | 10% Tween 20 aqueous solution *[16] |  | 5 |  |
|  | Water | 55 | 40 | 39.5 |
| Phase C | 5 wt % Mg ascorbate aqueous solution *[17] | 10 | 10 |  |

*[11] manufactured by Nikko Chemicals Co., Ltd. [product name: Carbopol 940]
*[12] FITC-labeled insulin manufactured by Sigma-Aldrich Corporation
*[13] manufactured by ITO, Inc. [product name: 13 Butimoist]
*[14] manufactured by Tokyo Chemical Industry Co., Ltd. [product name: Isopropyl Myristate]
*[15] manufactured by Nacalai Tesque, Inc. [product name: 1 mol/L-sodium hydroxide solution]
*[16] manufactured by Tokyo Chemical Industry Co., Ltd. [product name: Tween #20]
*[17] L-ascorbic acid phosphate Mg, L-ascorbic acid phosphate ester magnesium salt manufactured by Wako Pure Chemical Industries Ltd.

Example 8: Skin Permeability Test of Transdermally Absorbable Base Material

Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Examples 6 and 7 and Comparative Example 2 was placed in the donor phase of the vertical Franz type diffusion cell (refer to FIG. 2).

Figure 3:
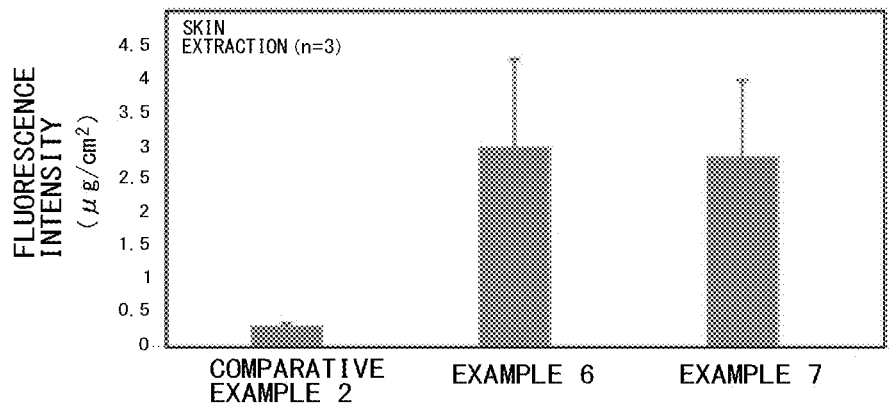
FIG. 3 is a diagram illustrating amounts of fluorescently-labeled insulin (fluorescence intensities in $\mu g/cm^2$) in extracted solutions of the skin after the skin permeability test (Example 8) conducted using transdermally absorbable base materials (gels) prepared in Examples 6 and 7 and Comparative Example 2.

The skin was taken out after 24 hours, and washed with the extractant [solution of PBS, acetonitrile, and methanol mixed at 2:1:1 (v/v/v)]. The liquid on the skin surface was wiped out with KimWipes (registered trademark). Then, the skin was cut into small pieces (16 pieces) with a utility knife, and put into a light-shielding microtube, to which 0.5 mL of the above-described extractant was added. The mixture was stirred with the vortex mixer for three hours, and the fluorescently-labeled insulin in the skin was extracted. Also, 1 mL of the receiver solution of the Franz type diffusion cell was put into the light-shielding microtube. The extracted solution thus obtained was filtered using a PTFE filter (0.20 μm), and then, the quantity of the fluorescently-labeled insulin in the solution was determined using the fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 3 illustrates the results obtained.

As illustrated in FIG. 3, the results were obtained, showing that the transdermally absorbable base materials of Examples 6 and 7 surpass the transdermally absorbable base material of Comparative Example 2 in transdermal absorption of insulin. No difference was found in density (roughly 0.1 μg/cm$^2$) of the fluorescently-labeled insulin in the receiver solution.

In this way, the result shows that the transdermally absorbable base material of the present invention is useful as a transdermally absorbable base material excellent in the transdermal absorbability thereof when the active ingredients, such as insulin, are blended therewith.

Example 9: Skin Permeability Test of Transdermally Absorbable Base Material

Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Examples 6 and 7 and Comparative Example 2 was placed in the donor phase of the vertical Franz type diffusion cell (refer to FIG. 2).

Figure 4:
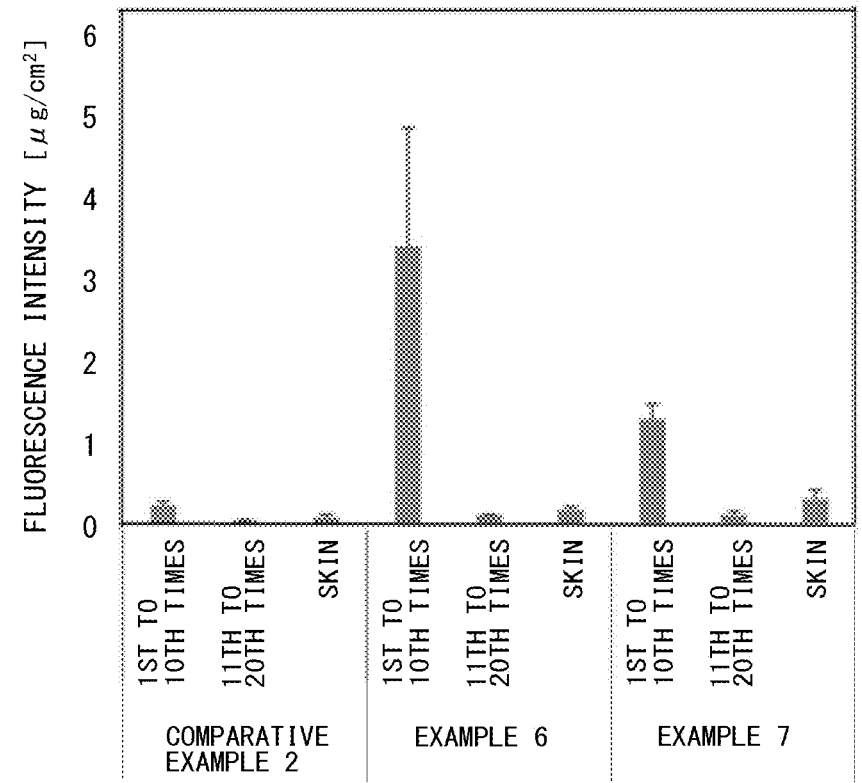
FIG. 4 is a diagram illustrating amounts of fluorescently-labeled insulin (fluorescence intensities in $\mu g/cm^2$) in extracted solutions of tapes obtained by tape stripping after the skin permeability test (Example 9) conducted using the transdermally absorbable base materials (gels) prepared in Examples 6 and 7 and Comparative Example 2.

The skin was taken out after 24 hours, and washed with the extractant [solution of PBS, acetonitrile, and methanol mixed at 2:1:1 (v/v/v)]. The liquid on the skin surface was wiped out with KimWipes (registered trademark). Then, tape stripping of the YMP skin was conducted (for the first to tenth times, and eleventh to twentieth times). Then, each of the tapes after being subjected to the tape stripping was put in a light-shielding microtube, to which 1 mL of the above-described extractant was added. The mixture was stirred with the vortex mixer for three hours, and the fluorescently-labeled insulin in the tape was extracted. The YMP skin after being subjected to the tape stripping 20 times was cut into small pieces (16 pieces) with a utility knife, and put into a light-shielding microtube, to which 1 mL of the above-described extractant was added. The mixture was stirred with the vortex mixer for three hours, and the fluorescently-labeled insulin in the skin was extracted. The extracted solution thus obtained was filtered using a PTFE filter (0.45 μm), and then, the quantity of the fluorescently-labeled insulin in the solution was determined using the fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 4 illustrates the results obtained.

As illustrated in FIG. 4, the results were obtained, showing that the transdermally absorbable base materials of Examples 6 and 7 surpass the transdermally absorbable base material of Comparative Example 2 in transdermal absorption of insulin. The amount of insulin for the first to tenth times of the stripping was high, which suggested that the insulin penetrated to an upper layer portion of the stratum corneum.

In this way, the result shows that the transdermally absorbable base material of the present invention is useful as a transdermally absorbable base material excellent in the transdermal absorbability thereof when the active ingredients, such as insulin, are blended therewith.

Examples 10 and 11 and Comparative Example 3: Preparation of Transdermally Absorbable Base Material Using Premix According to Table 4 below, Phase A (premix prepared in Example 1) was weighed out into a sample tube No. 5, and heated in a water bath (at a set temperature of 85° C.) to be uniformly dissolved.

The ingredients of Phase B were weighed out into another Maruemu sample tube No. 5 having therein a stirrer chip, and heated in a water bath (at a set temperature of 85° C.). Phase A was added to Phase B, mixed while being heated and stirred for roughly 30 seconds. Then, the mixture was cooled while being stirred until the liquid temperature reached roughly 60° C.

For each of Examples 10 and 11, the ingredients of Phase C were weighed out into still another sample tube No. 5, and heated to a liquid temperature of roughly 60° C. When the liquid temperature of (Phase A+Phase B) described above reached 60° C., Phase C having a liquid temperature of roughly 60° C. was added thereto, and the mixture was stirred for roughly 30 seconds, and then left at rest and cooled to be formed into a gel (transdermally absorbable base material).

For Comparative Example 3, after the liquid temperature reached roughly 60° C., the mixture was left at rest and cooled to be formed into a gel (transdermally absorbable base material). Each of the prepared transdermally absorbable base materials contains 0.1% by mass of the fluorescently-labeled insulin (FITC-labeled insulin).

TABLE 4

| | Ingredient (g) | Example 10 | Example 11 | Comparative Example 3 |
|---|---|---|---|---|
| Phase A | Premix | 5 | 5 | |
| | 1.0 wt % Carbopol *[18] | | | 50 |
| Phase B | 0.333 wt % FITC-labeled insulin aqueous solution *[19] | 30 | 30 | 30 |
| | 1,3-butanediol *[20] | 20 | 20 | |
| | IPM *[21] | | 10 | |
| | 1M NaOH *[22] | | | 0.5 |
| | 10% Tween 20 aqueous solution *[23] | | 5 | |
| | Water | 35 | 20 | 19.5 |
| Phase C | 5 wt % Mg ascorbate aqueous solution *[24] | 10 | 10 | |

*[18] manufactured by Nikko Chemicals Co., Ltd. [product name: Carbopol 940]
*[19] FITC-labeled insulin prepared in Preparation Example 1
*[20] manufactured by ITO, Inc. [product name: 13 Butimoist]
*[21] manufactured by Tokyo Chemical Industry Co., Ltd. [product name: Isopropyl Myristate]
*[22] manufactured by Nacalai Tesque, Inc. [product name: 1 mol/L-sodium hydroxide solution]
*[23] manufactured by Tokyo Chemical Industry Co., Ltd. [product name: Tween #20]
*[24] L-ascorbic acid phosphate Mg, L-ascorbic acid phosphate ester magnesium salt manufactured by Wako Pure Chemical Industries Ltd.

Example 12: Skin Permeability Test of Transdermally Absorbable Base Material

Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Examples 10 and 11 and Comparative Example 3 was placed in the donor phase of the vertical Franz type diffusion cell (refer to FIG. 2).

Figure 5:
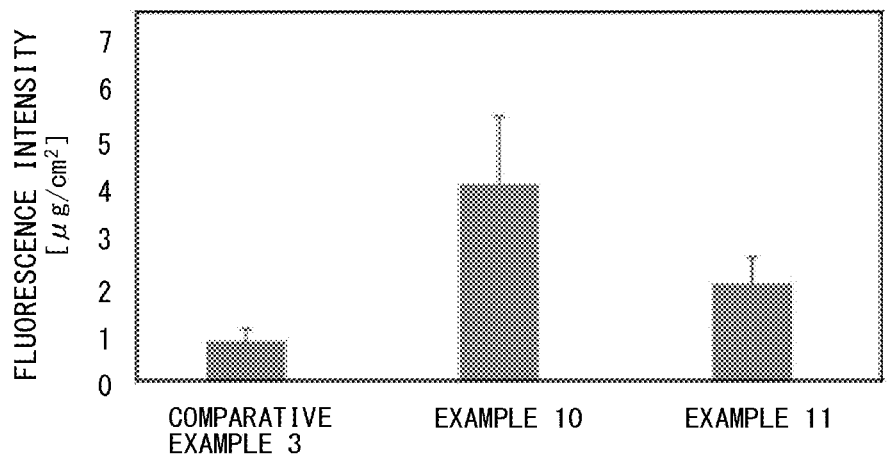
FIG. 5 is a diagram illustrating amounts of fluorescently-labeled insulin (fluorescence intensities in $\mu g/cm^2$) in extracted solutions of the skin after the skin permeability test (Example 12) conducted using transdermally absorbable base materials (gels) prepared in Examples 10 and 11 and Comparative Example 3.

The skin was taken out after 24 hours, and washed with the extractant [solution of PBS, acetonitrile, and methanol mixed at 2:1:1 (v/v/v)]. The liquid on the skin surface was wiped out with KimWipes (registered trademark). Then, the skin was cut into small pieces (16 pieces) with a utility knife, and put into a light-shielding microtube, to which 0.5 mL of the above-described extractant was added. The mixture was stirred with the vortex mixer for three hours, and the fluorescently-labeled insulin in the skin was extracted. The extracted solution thus obtained was filtered using a PTFE filter (0.45 μm), and then, the quantity of the fluorescently-labeled insulin in the solution was determined using the fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 5 illustrates the results obtained.

As illustrated in FIG. 5, the results were obtained, showing that the transdermally absorbable base materials of Examples 10 and 11 surpass the transdermally absorbable base material of Comparative Example 3 in transdermal absorption of insulin.

In this way, the result shows that the transdermally absorbable base material of the present invention is useful as a transdermally absorbable base material excellent in the transdermal absorbability thereof when the active ingredients, such as insulin, are blended therewith.

Moreover, the following test was conducted to examine the effect of the polyoxyethylene lauryl ether in the premix of the present invention (Examples 13 and 14).

Example 13 and Comparative Example 4: Preparation of Transdermally Absorbable Base Material Using Premix According to Table 5 below, Phase A (premix prepared in Example 1) was weighed out into a sample tube No. 5, and heated in a water bath (at a set temperature of 85° C.) to be uniformly dissolved.

The ingredients of Phase B were weighed out into another Maruemu sample tube No. 5 having therein a stirrer chip, and heated in a water bath (at a set temperature of 85° C.). Phase A was added to Phase B, mixed while being heated and stirred for roughly 30 seconds. Then, the mixture was cooled while being stirred until the liquid temperature reached roughly 60° C.

The ingredients of Phase C were weighed out into still another sample tube No. 5, and heated to a liquid temperature of roughly 60° C. When the liquid temperature of mixture of Phase A and Phase B described above reached 60° C., Phase C having a liquid temperature of roughly 60° C. was added thereto, and the mixture was stirred for roughly 30 seconds, and then left at rest and cooled to be formed into a gel (transdermally absorbable base material).

For Comparative Example 4, the ingredients of Phase B were weighed out into another Maruemu sample tube No. 5 having therein a stirrer chip, and heated in a water bath (at a set temperature of 85° C.). Phase B was mixed while being heated and stirred for roughly 30 seconds, and then cooled while being stirred until the liquid temperature reached roughly 60° C. After the liquid temperature reached roughly 60° C., Phase B was left at rest and cooled to be formed into a gel (transdermally absorbable base material). Each of the prepared transdermally absorbable base materials contains 0.1% by mass of the fluorescently-labeled insulin (FITC-labeled insulin).

TABLE 5

|  | Ingredient (g) | Example 13 | Comparative Example 4 |
|---|---|---|---|
| Phase A | Premix | 5 | |
| Phase B | 0.333 wt % FITC-labeled insulin aqueous solution *[25] | 30 | 30 |
| | 1,3-butanediol *[26] | 20 | |
| | Polyoxyethylene lauryl ether *[27] | | 0.4 |
| | Water | 35 | 69.6 |
| Phase C | 5 wt % Mg ascorbate aqueous solution *[28] | 10 | |

*[25] FITC-labeled insulin prepared in Preparation Example 1
*[26] manufactured by ITO, Inc. [product name: 13 Butimoist]
*[27] Polyoxyethylene lauryl ether BL-4.2 3458 manufactured by Nikko Chemicals Co., Ltd.
*[28] L-ascorbic acid phosphate Mg, L-ascorbic acid phosphate ester magnesium salt manufactured by Wako Pure Chemical Industries Ltd.

Example 14: Skin Permeability Test of Transdermally Absorbable Base Material Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Example 13 and Comparative Example 4 was placed in the donor phase of the vertical Franz type diffusion cell (refer to FIG. 2).

Figure 6:
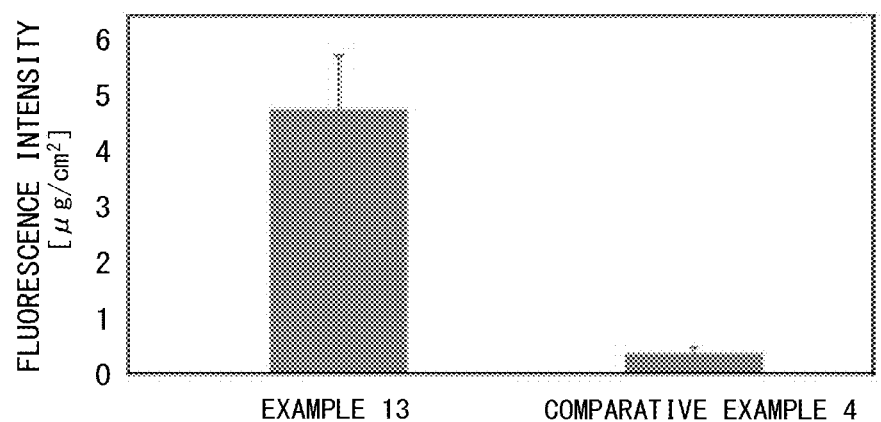
FIG. 6 is a diagram illustrating amounts of fluorescently-labeled insulin (fluorescence intensities in $\mu g/cm^2$) in extracted solutions of the skin after the skin permeability test (Example 14) conducted using transdermally absorbable base materials (gels) and polyoxylauryl ether prepared in Example 13 and Comparative Example 4.

The skin was taken out after 24 hours, and washed with the extractant [solution of PBS, acetonitrile, and methanol mixed at 2:1:1 (v/v/v)]. The liquid on the skin surface was wiped out with KimWipes (registered trademark). Then, the skin was cut into small pieces (16 pieces) with a utility knife, and put into a light-shielding microtube, to which 0.5 mL of the above-described extractant was added. The mixture was stirred with the vortex mixer for three hours, and the fluorescently-labeled insulin in the skin was extracted. The extracted solution thus obtained was filtered using a PTFE filter (0.45 μm), and then, the quantity of the fluorescently-labeled insulin in the solution was determined using the fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 6 illustrates the results obtained.

As illustrated in FIG. 6, no transdermal absorption enhancing effect of insulin was found to be provided by 0.4% polyoxyethylene lauryl ether itself contained in the premix.

Example 15: Preparation of Premix

The Pal-GH obtained in Synthesis Example 1 above, 1,2-hexanediol, stearic acid, and water were weigh out so as to form a composition (% by mass) illustrated in Table 6, and charged into a sample tube (No. 7 manufactured by Maruemu Corporation). The mixture was heated and stirred at 80° C. to obtain a Pal-GH dispersion liquid (premix). The stirring was performed at 200 rpm using a LABORATORY HIGH MIXER manufactured by AS ONE Corporation.

This premix did not contain the surfactant, which was added when the transdermally absorbable base material was prepared afterward.

TABLE 6

| Ingredient | Premix composition (% by mass) |
|---|---|
| Pal-GH | 6.0 |
| 1,2-hexanediol *[29] | 20.0 |
| Stearic acid *[29] | 0.6 |
| Water | Rest |

*[29] manufactured by Wako Pure Chemical Industries Ltd.

Examples 16 and 17 and Comparative Example 5: Preparation of Transdermally Absorbable Base Material Using Premix According to Table 7 below, Phase A (premix prepared in Example 15) was weighed out into a sample tube No. 5, and heated in a water bath (at a set temperature of 85° C.) to be uniformly dissolved.

The ingredients of Phase B were weighed out into another Maruemu sample tube No. 5 having therein a stirrer chip, and heated in a water bath (at a set temperature of 85° C.). Phase A was added to Phase B, mixed while being heated and stirred for roughly 30 seconds. Then, the mixture was cooled while being stirred until the liquid temperature reached roughly 60° C. After the liquid temperature reached roughly 60° C., the mixture was left standing as it was and cooled to be formed into a gel (transdermally absorbable base material). Each of the prepared transdermally absorbable base materials contains 0.1% by mass of the fluorescently-labeled insulin (FITC-labeled insulin).

TABLE 7

| | Ingredient (g) | Example 16 | Example 17 | Comparative Example 5 |
|---|---|---|---|---|
| Phase A | Premix | 5 | 5 | |
| | 1.0 wt % Carbopol *[30] | | | 60 |
| Phase B | 0.3 wt % FITC-labeled insulin aqueous solution *[31] | 34 | 34 | 34 |
| | 3 wt % propylene glycol alginate *[32] | 10 | 10 | |
| | IPM *[33] | | 10 | |
| | 1M NaOH *[34] | | | 0.47 |
| | 10% Tween 20 aqueous solution *[35] | | 5 | |
| | Water | 51 | 36 | 5.53 |

*[30] manufactured by Nikko Chemicals Co., Ltd. [product name: Carbopol 940]
*[31] FITC-labeled insulin manufactured by Sigma-Aldrich Corporation
*[32] aqueous solution prepared using propylene glycol alginate manufactured by Wako Pure Chemical Industries Ltd.
*[33] manufactured by Tokyo Chemical Industry Co., Ltd. [product name: Isopropyl Myristate]
*[34] manufactured by Nacalai Tesque, Inc. [product name: 1 mol/L-sodium hydroxide solution]
*[35] manufactured by Tokyo Chemical Industry Co., Ltd. [product name: Tween #20]

Example 18: Skin Permeability Test of Transdermally Absorbable Base Material Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 5.0 mL of phosphate buffered saline (PBS of pH 7.4, stirred at 500 rpm) was added, and the above-described YMP skin (temperature of PBS on skin surface: 32.5° C.) was set. Each of the gels (200 mg) prepared in Examples 16 and 17 and Comparative Example 5 was placed in the donor phase of the vertical Franz type diffusion cell (refer to FIG. 2).

Figure 7:
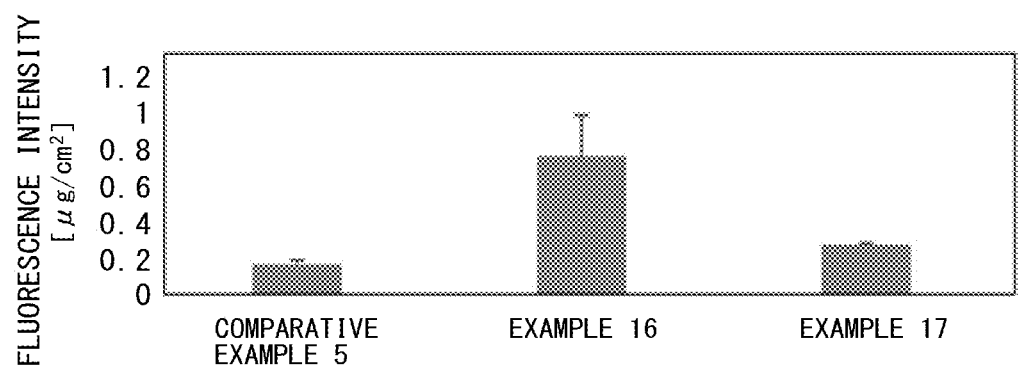
FIG. 7 is a diagram illustrating amounts of fluorescently-labeled insulin (fluorescence intensities in $\mu g/cm^2$) in extracted solutions of the skin after the skin permeability test (Example 18) conducted using transdermally absorbable base materials (gels) prepared in Examples 16 and 17 and Comparative Example 5.

The skin was taken out after 24 hours, and washed with the extractant [solution of PBS, acetonitrile, and methanol mixed at 2:1:1 (v/v/v)]. The liquid on the skin surface was wiped out with KimWipes (registered trademark). Then, the skin was cut into small pieces (16 pieces) with a utility knife, and put into a light-shielding microtube, to which 0.5 mL of the above-described extractant was added. The mixture was stirred with the vortex mixer for three hours, and the fluorescently-labeled insulin in the skin was extracted. Also, 1 mL of the receiver solution of the Franz type diffusion cell was put into the light-shielding microtube. The extracted solution thus obtained was filtered using a PTFE filter (0.20 μm), and then, the quantity of the fluorescently-labeled insulin in the solution was determined using the fluorescence spectrometer LS-55 (manufactured by PerkinElmer, Inc.) (each calculated as the average value of three tests). The fluorescence spectrometer measurement was made at an excitation wavelength of 495 nm and a measurement wavelength of 521 nm. FIG. 7 illustrates the results obtained.

As illustrated in FIG. 7, the results were obtained, showing that the transdermally absorbable base materials of Examples 16 and 17 surpass the transdermally absorbable base material of Comparative Example 5 in transdermal absorption of insulin. No difference was found in density (roughly 0.2 μg/cm$^2$) of the fluorescently-labeled insulin in the receiver solution.

In this way, the result shows that the transdermally absorbable base material of the present invention is useful as a transdermally absorbable base material excellent in the transdermal absorbability thereof when the active ingredients, such as insulin, are blended therewith.

Figure 8:
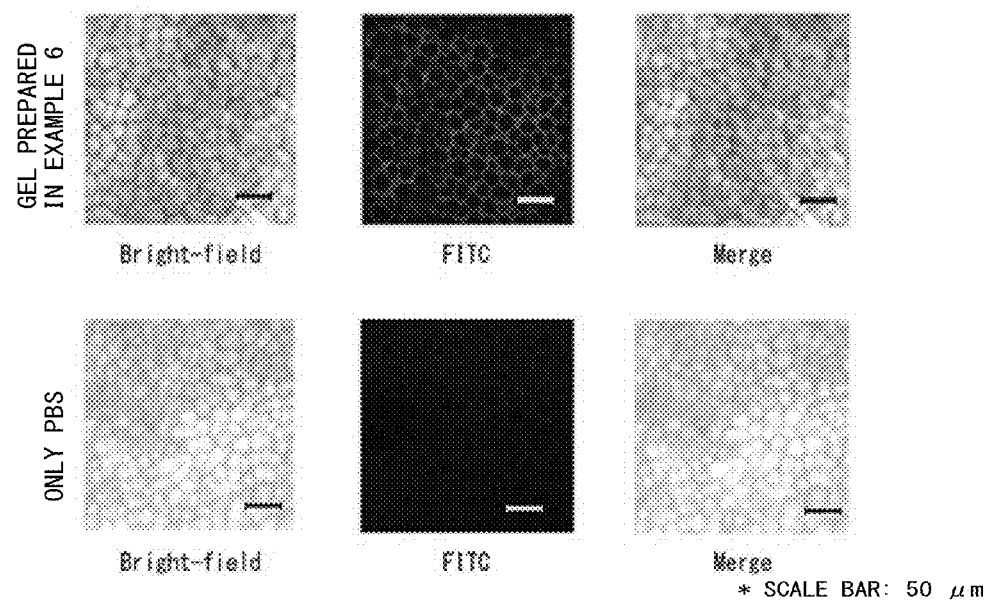
FIG. 8 depicts confocal micrographs illustrating permeability through the skin of a mouse ear taken using the transdermally absorbable base material (gel) prepared in Example 6.

Example 19: Observation of Fluorescently-Labeled Insulin Penetration into Mouse Ear An ear of a mouse (Kyudo Co., Ltd.) stored at −80° C. was thawed at room temperature (roughly 25° C.), and was then cut out into a size of roughly 5 mm square to serve as a specimen, to which 50 mg of the gel containing the Pal-GH gel premix prepared in Example 6 was added. After 4 hours, the gel was removed from the specimen. Subsequently, the specimen was placed on a glass slide, and several drops of isopropyl myristate (IPM) were dropped thereon. The specimen was covered with a cover glass to form a prepared slide, and was observed with a confocal microscope (LSM 700 manufactured by Carl Zeiss Microscopy GmbH). Instead of the transdermally absorbable base material, 10 μL of phosphate buffered saline (PBS) was added to prepare a prepared slide in the same way as a reference, which was compared with the specimen described above. FIG. 8 illustrates the results (in FIG. 8, Bright-field, FITC, and Merge represent a bright-field image, a fluorescence image, and a combined image thereof, respectively). From FIG. 8, a state was observed where the use of the transdermally absorbable base material prepared in Example 6 caused the insulin to penetrate through intracellular pathways.

Figure 9:
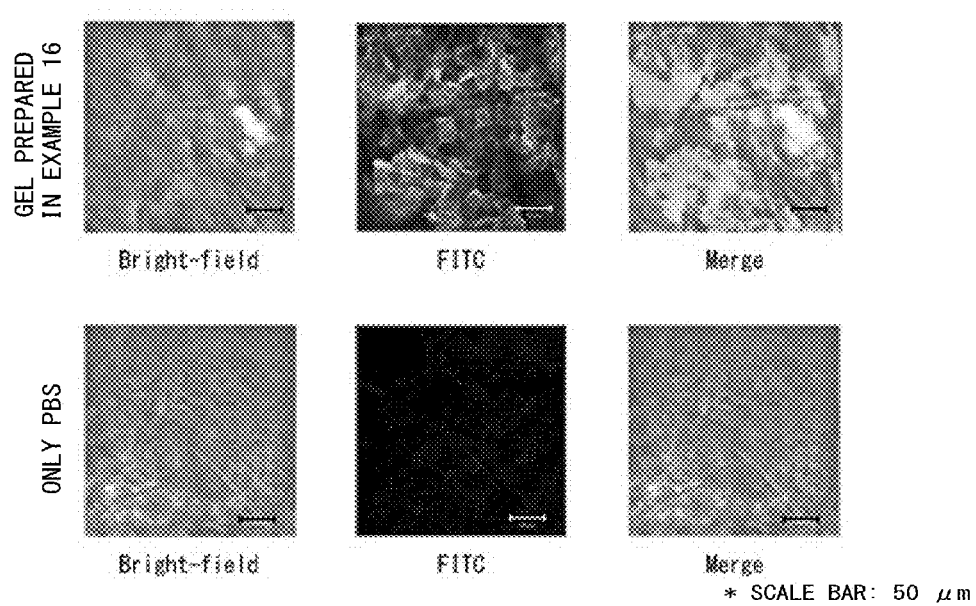
FIG. 9 depicts confocal micrographs illustrating permeability through the skin of a mouse ear taken using the transdermally absorbable base material (gel) prepared in Example 16.

Example 20: Observation of Fluorescently-Labeled Insulin Penetration into Mouse Ear An ear of a mouse (Kyudo Co., Ltd.) stored at −80° C. was thawed at room temperature (roughly 25° C.), and was then cut out into a size of roughly 5 mm square to serve as a specimen, to which 50 mg of the gel prepared in Example 16 was added. After 4 hours, the gel was removed from the specimen. Subsequently, the specimen was placed on a glass slide, and several drops of isopropyl myristate (IPM) were dropped thereon. The specimen was covered with a cover glass to form a prepared slide, and was observed with the confocal microscope (LSM 700 manufactured by Carl Zeiss Microscopy GmbH). Instead of the transdermally absorbable base material, 10 μL of phosphate buffered saline (PBS) was added, to prepare a prepared slide in the same way as a reference, which was compared with the specimen described above. FIG. 9 illustrates the results (in FIG. 9, Bright-field, FITC, and Merge represent a bright-field image, a fluorescence image, and a combined image thereof, respectively).

From FIG. 9, a state was observed where the use of the transdermally absorbable base material prepared in Example 16 caused the insulin to penetrate through intracellular pathways.

[Observation of Fluorescently-Labeled Insulin Penetration into YMP Skin]

Yucatan Micro Pig (YMP) skin (by Charles River Laboratories Japan, Inc.) stored at −80° C. was thawed at room temperature (roughly 25° C.), and was then subjected to the fat removal (to have a skin thickness of roughly 2 mm). Thus, the YMP skin of roughly 2 cm square was prepared.

To a receiver phase of the vertical Franz type diffusion cell (effective area: 0.785 cm$^2$), 4.0 mL of phosphate buffered saline (PBS of pH 7.4, stirred at 500 rpm) was added, and the above-described YMP skin (temperature of PBS on skin surface: 32.5° C.) was set. Then, air in the vertical Franz type diffusion cell was removed, and 1 mL of the PBS was added. Then, the gel (200 mg) prepared in Example 16 was added. After 24 hours, the gel was removed, and the YMP skin was subjected to permeation in a 4% paraformaldehyde fixative solution (manufactured by Muto Pure Chemicals Co., Ltd.) for 5 hours to be fixed. Then, the skin was placed in a plastic base mold, into which O. C. T. compound (manufactured by Sakura Finetek Japan Co., Ltd.) was added to freeze the skin with liquid nitrogen. The skin was kept in a deep freezer (−80° C.). Then, a round chuck was attached to the frozen skin, which was cut out into a frozen section having a thickness of 12 μm using a cryostat microtome, and stuck onto a prepared slide. Several drops of the PBS solution were dropped onto the prepared slide, and the O. C. T. compound was removed. Then, several drops of the PBS solution were dropped again, and a cover glass was set so as not to let air enter while the prepared slide was wet. The prepared slide was observed with a fluorescence microscope. As comparison, the above-described operations were performed using only an insulin aqueous solution (containing 34 wt % of 0.3 wt % FITC-labeled insulin aqueous solution and 66 wt % of water) (200 mg) instead of the transdermally absorbable base material and phosphate buffered saline (PBS) as a reference, and the prepared slides were observed with the fluorescence microscope.

Figure 10:
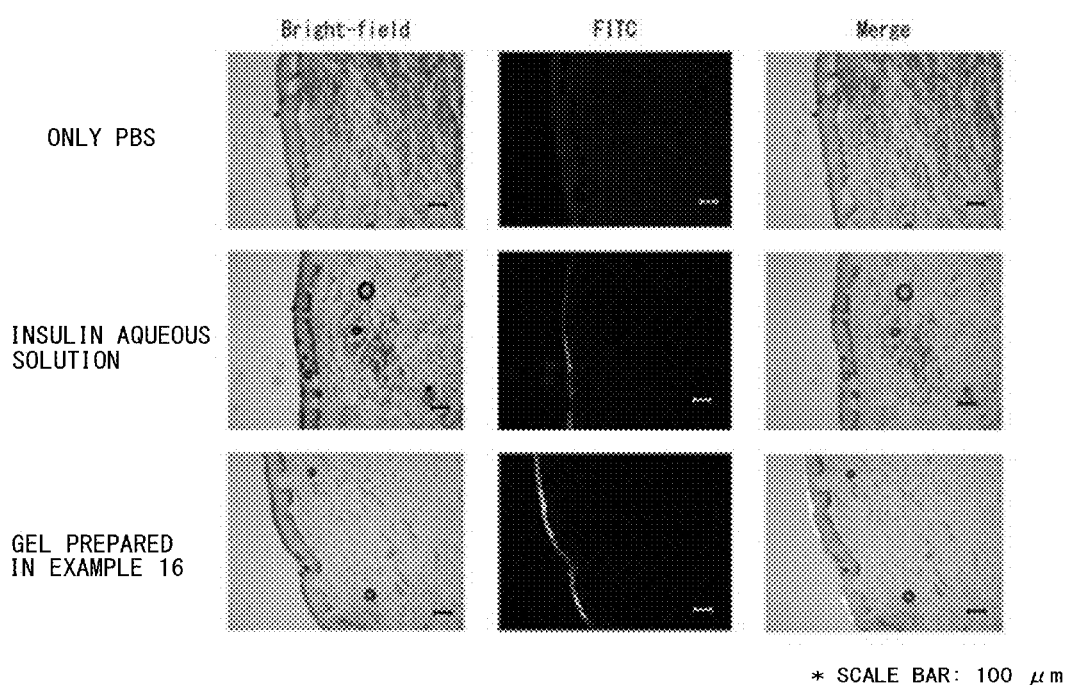
FIG. 10 depicts fluorescence micrographs illustrating permeability through YMP skin taken using the transdermally absorbable base material (gel) prepared in Example 16.

FIG. 10 illustrates fluorescence micrographs of the observed YMP skins (in FIG. 10, Bright-field, FITC, and Merge represent a bright-field image, a fluorescence image, and a combined image thereof, respectively). It was found from FIG. 10 that the most intense fluorescence was emitted from the YMP skin to which the gel prepared in Example 16 was applied. This suggested that the insulin penetrated to the stratum corneum.

The invention claimed is:

1. A method of transdermally absorbing an active component, the method comprising:

applying a composition comprising a lipid peptide compound of Formula (1) or pharmaceutically usable salts thereof, a surfactant, an 1,2-alkanediol or a glycerin, at least one fatty acid, water, and the active component to skin,

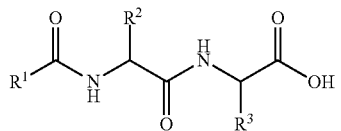
(1)

wherein $R^1$ is a $C_{9-23}$ aliphatic group; $R^2$ is a hydrogen atom or a $C_{1-4}$ alkyl group that optionally has a branched chain having a carbon atom number of 1 or 2; $R^3$ is a —(CH$_2$)—X group; n is a number of 1 to 4; and X is amino group, guanidino group, —CONH$_2$ group, or a 5-membered cyclic group optionally having 1 to 3 nitrogen atoms, a 6-membered cyclic group optionally having 1 to 3 nitrogen atoms, or a condensed heterocyclic group constituted by a 5-membered cyclic group and a 6-membered cyclic group which optionally have 1 to 3 nitrogen atoms;

wherein the active component is selected from hyaluronic acid and insulin, wherein the at least one fatty acid is selected from among the group consisting of capric acid, myristic acid, palmitic acid, and stearic acid, and wherein the surfactant is at least one of an ethylene glycol alkyl ether, a phospholipid, and a polyglycerin fatty acid ester; and allowing the active component to transdermally absorb into the skin.

2. The method according to claim 1, wherein in Formula (1), $R^1$ is a linear aliphatic group having a carbon atom number of 15, $R^2$ is a hydrogen atom, and $R^3$ is 4-imidazole methyl group.

* * * * *